(12) United States Patent
Baez, Jr.

(10) Patent No.: US 10,881,280 B2
(45) Date of Patent: Jan. 5, 2021

(54) MANUALLY AND ROBOTICALLY CONTROLLABLE MEDICAL INSTRUMENTS

(71) Applicant: Auris Health, Inc., Redwood City, CA (US)

(72) Inventor: Luis Andrade Baez, Jr., Mountain View, CA (US)

(73) Assignee: Auris Health, Inc., Redwood City, CA (US)

(*) Notice: Subject to any disclaimer, the term of this patent is extended or adjusted under 35 U.S.C. 154(b) by 0 days.

(21) Appl. No.: 16/548,520

(22) Filed: Aug. 22, 2019

(65) Prior Publication Data

US 2020/0060516 A1    Feb. 27, 2020

Related U.S. Application Data

(60) Provisional application No. 62/887,508, filed on Aug. 15, 2019, provisional application No. 62/722,665, filed on Aug. 24, 2018.

(51) Int. Cl.
*A61B 34/20* (2016.01)
*A61B 1/005* (2006.01)
(Continued)

(52) U.S. Cl.
CPC .......... *A61B 1/0057* (2013.01); *A61B 1/0053* (2013.01); *A61B 1/00149* (2013.01);
(Continued)

(58) Field of Classification Search
CPC ... A61B 1/0052; A61B 1/0057; A61B 1/0051; A61B 1/008; A61B 34/30; A61B 34/71; A61B 2034/301
(Continued)

(56) References Cited

U.S. PATENT DOCUMENTS

| 5,669,876 A | 9/1997 | Schechter et al. |
| 8,021,326 B2 * | 9/2011 | Moll ...................... A61B 34/20 600/114 |

(Continued)

FOREIGN PATENT DOCUMENTS

| EP | 2 615 992 | 7/2016 |
| WO | WO 10/127162 | 11/2010 |

(Continued)

OTHER PUBLICATIONS

International Search Report and Written Opinion in application No. PCT/US2019/47753, dated Feb. 7, 2020.

*Primary Examiner* — Matthew J Kaszetjna
(74) *Attorney, Agent, or Firm* — Knobbe Martens Olson & Bear LLP

(57) ABSTRACT

Certain aspects relate to manually and robotically controllable medical instruments. A manually and robotically controllable medical instrument can include an elongated shaft articulable by pull wires. The elongated shaft can be connected to an instrument handle that attaches to an instrument drive mechanism. The instrument handle can include a pulley assembly on which the pull wires can be mounted. Rotation of the pulley assembly can actuate the pull wires to cause articulation of the elongated shaft. The medical instrument also includes a manual drive input connected to the pulley assembly such that manual actuation of the manual drive input causes rotation of the first pulley assembly and a robotic drive input configured to engage with a robotic drive output of the instrument drive mechanism such that rotation of the first robotic drive output causes rotation of the pulley assembly.

18 Claims, 37 Drawing Sheets

(51) Int. Cl.
*A61B 50/13* (2016.01)
*A61B 10/04* (2006.01)
*A61B 1/307* (2006.01)
*A61B 1/00* (2006.01)
*A61B 1/267* (2006.01)

(52) U.S. Cl.
CPC ............ *A61B 1/2676* (2013.01); *A61B 1/307* (2013.01); *A61B 10/04* (2013.01); *A61B 34/20* (2016.02); *A61B 50/13* (2016.02); *A61B 2010/045* (2013.01); *A61B 2034/2051* (2016.02)

(58) Field of Classification Search
USPC .................................................. 600/140–149
See application file for complete search history.

(56) References Cited

U.S. PATENT DOCUMENTS

| | | | |
|---|---|---|---|
| 9,173,713 | B2 | 11/2015 | Hart et al. |
| 9,259,274 | B2 | 2/2016 | Prisco |
| 9,302,702 | B1 | 4/2016 | Schepmann |
| 9,504,604 | B2 | 11/2016 | Alvarez |
| 9,561,083 | B2 | 2/2017 | Yu et al. |
| 9,622,827 | B2 | 4/2017 | Yu et al. |
| 9,636,184 | B2 | 5/2017 | Lee et al. |
| 9,713,509 | B2 | 7/2017 | Schuh et al. |
| 9,717,563 | B2 | 8/2017 | Tognaccini |
| 9,727,963 | B2 | 8/2017 | Mintz et al. |
| 9,737,371 | B2 | 8/2017 | Romo et al. |
| 9,737,373 | B2 | 8/2017 | Schuh |
| 9,744,335 | B2 | 8/2017 | Jiang |
| 9,763,741 | B2 | 9/2017 | Alvarez et al. |
| 9,788,910 | B2 | 10/2017 | Schuh |
| 9,839,481 | B2 | 12/2017 | Blumenkranz et al. |
| 9,844,412 | B2 | 12/2017 | Bogusky et al. |
| 9,867,635 | B2 | 1/2018 | Alvarez et al. |
| 9,918,681 | B2 | 3/2018 | Wallace et al. |
| 9,931,025 | B1 | 4/2018 | Graetzel et al. |
| 9,949,749 | B2 | 4/2018 | Noonan et al. |
| 9,955,986 | B2 | 5/2018 | Shah |
| 9,962,228 | B2 | 5/2018 | Schuh et al. |
| 9,980,785 | B2 | 5/2018 | Schuh |
| 9,993,313 | B2 | 6/2018 | Schuh et al. |
| 10,016,900 | B1 | 7/2018 | Meyer et al. |
| 10,022,192 | B1 | 7/2018 | Ummalaneni |
| 10,080,576 | B2 | 9/2018 | Romo et al. |
| 10,136,959 | B2 | 11/2018 | Mintz et al. |
| 10,145,747 | B1 | 12/2018 | Lin et al. |
| 10,149,720 | B2 | 12/2018 | Romo |
| 10,159,532 | B1 | 12/2018 | Ummalaneni et al. |
| 10,159,533 | B2 | 12/2018 | Moll et al. |
| 10,169,875 | B2 | 1/2019 | Mintz et al. |
| 10,213,264 | B2 | 2/2019 | Tanner et al. |
| 10,219,874 | B2 | 3/2019 | Yu et al. |
| 10,231,793 | B2 | 3/2019 | Romo |
| 10,231,867 | B2 | 3/2019 | Alvarez et al. |
| 10,244,926 | B2 | 4/2019 | Noonan et al. |
| 10,285,574 | B2 | 5/2019 | Landey et al. |
| 10,299,870 | B2 | 5/2019 | Connolly et al. |
| 10,314,463 | B2 | 6/2019 | Agrawal et al. |
| 10,383,765 | B2 | 8/2019 | Alvarez et al. |
| 10,398,518 | B2 | 9/2019 | Yu et al. |
| 10,405,939 | B2 | 9/2019 | Romo et al. |
| 10,405,940 | B2 | 9/2019 | Romo |
| 10,426,559 | B2 | 10/2019 | Graetzel et al. |
| 10,426,661 | B2 | 10/2019 | Kintz |
| 10,434,660 | B2 | 10/2019 | Meyer |
| 2002/0128535 | A1 | 9/2002 | Kikuchi |
| 2003/0181809 | A1 | 9/2003 | Hall et al. |
| 2007/0232856 | A1* | 10/2007 | Ueno ................. A61B 1/00039 600/118 |
| 2008/0046122 | A1 | 2/2008 | Manzo et al. |
| 2008/0140087 | A1 | 6/2008 | Barbagli et al. |
| 2009/0062611 | A1 | 3/2009 | Toyama |
| 2009/0259099 | A1 | 10/2009 | Zhou et al. |
| 2010/0082041 | A1 | 4/2010 | Prisco |
| 2010/0198170 | A1 | 8/2010 | Umeda et al. |
| 2010/0204713 | A1 | 8/2010 | Ruiz |
| 2010/0228266 | A1 | 9/2010 | Hourtash |
| 2011/0015484 | A1 | 1/2011 | Alvarez et al. |
| 2012/0071894 | A1 | 3/2012 | Tanner et al. |
| 2012/0221007 | A1 | 8/2012 | Batten et al. |
| 2012/0239060 | A1 | 9/2012 | Orban, III |
| 2012/0302869 | A1 | 11/2012 | Koyrakh |
| 2013/0123580 | A1* | 5/2013 | Peters ................. A61B 1/0057 600/118 |
| 2013/0209208 | A1 | 8/2013 | Bailey |
| 2013/0218005 | A1 | 8/2013 | Desai |
| 2013/0274783 | A1 | 10/2013 | Wynberg |
| 2014/0001235 | A1 | 1/2014 | Shelton, IV |
| 2014/0142591 | A1 | 5/2014 | Alvarez et al. |
| 2014/0257333 | A1 | 9/2014 | Blumenkranz |
| 2014/0309625 | A1 | 10/2014 | Okamoto et al. |
| 2014/0357984 | A1 | 12/2014 | Wallace et al. |
| 2014/0364870 | A1 | 12/2014 | Alvarez et al. |
| 2015/0119645 | A1 | 4/2015 | Baldwin |
| 2015/0150636 | A1 | 6/2015 | Hagn et al. |
| 2015/0305650 | A1 | 10/2015 | Hunter |
| 2015/0311838 | A1 | 10/2015 | Moule |
| 2016/0001038 | A1 | 1/2016 | Romo et al. |
| 2016/0166320 | A1 | 6/2016 | Ciulla |
| 2016/0270865 | A1 | 9/2016 | Landey et al. |
| 2016/0287279 | A1 | 10/2016 | Bovay et al. |
| 2017/0007337 | A1 | 1/2017 | Dan |
| 2017/0106904 | A1 | 4/2017 | Hanson |
| 2017/0119481 | A1 | 5/2017 | Romo et al. |
| 2017/0135718 | A1 | 5/2017 | Lyons |
| 2017/0165011 | A1 | 6/2017 | Bovay et al. |
| 2017/0172673 | A1 | 6/2017 | Yu et al. |
| 2017/0209162 | A1 | 6/2017 | Sperry |
| 2017/0189118 | A1 | 7/2017 | Chopra |
| 2017/0202627 | A1 | 7/2017 | Sramek et al. |
| 2017/0209073 | A1 | 7/2017 | Sramek et al. |
| 2017/0231647 | A1 | 8/2017 | Saunders |
| 2017/0245854 | A1 | 8/2017 | Zemlok |
| 2017/0290631 | A1 | 10/2017 | Lee et al. |
| 2017/0326337 | A1 | 11/2017 | Romoscanu |
| 2017/0333679 | A1 | 11/2017 | Jiang |
| 2017/0340396 | A1 | 11/2017 | Romo et al. |
| 2017/0367782 | A1 | 12/2017 | Schuh et al. |
| 2018/0025666 | A1 | 1/2018 | Ho et al. |
| 2018/0169671 | A1 | 6/2018 | Winter |
| 2018/0177556 | A1 | 6/2018 | Noonan et al. |
| 2018/0214011 | A1 | 8/2018 | Graetzel et al. |
| 2018/0221038 | A1 | 8/2018 | Noonan et al. |
| 2018/0221039 | A1 | 8/2018 | Shah |
| 2018/0250083 | A1 | 9/2018 | Schuh et al. |
| 2018/0271616 | A1 | 9/2018 | Schuh et al. |
| 2018/0279852 | A1 | 10/2018 | Rafii-Tari et al. |
| 2018/0280660 | A1 | 10/2018 | Landey et al. |
| 2018/0289394 | A1 | 10/2018 | Shah |
| 2018/0289431 | A1 | 10/2018 | Draper et al. |
| 2018/0325499 | A1 | 11/2018 | Landey et al. |
| 2018/0333044 | A1 | 11/2018 | Jenkins |
| 2018/0360435 | A1 | 12/2018 | Roma |
| 2019/0000559 | A1 | 1/2019 | Berman et al. |
| 2019/0000560 | A1 | 1/2019 | Berman et al. |
| 2019/0000576 | A1 | 1/2019 | Mintz et al. |
| 2019/0083183 | A1 | 3/2019 | Moll et al. |
| 2019/0105776 | A1 | 4/2019 | Ho et al. |
| 2019/0107454 | A1 | 4/2019 | Lin |
| 2019/0110839 | A1 | 4/2019 | Rafii-Tari et al. |
| 2019/0110843 | A1 | 4/2019 | Ummalaneni et al. |
| 2019/0151148 | A1 | 4/2019 | Alvarez et al. |
| 2019/0167366 | A1 | 6/2019 | Ummalaneni |
| 2019/0175009 | A1 | 6/2019 | Mintz |
| 2019/0175062 | A1 | 6/2019 | Rafii-Tari et al. |
| 2019/0175287 | A1 | 6/2019 | Hill et al. |
| 2019/0175799 | A1 | 6/2019 | Hsu |
| 2019/0183585 | A1 | 6/2019 | Rafii-Tari et al. |
| 2019/0183587 | A1 | 6/2019 | Rafii-Tari et al. |
| 2019/0216548 | A1 | 7/2019 | Ummalaneni |

(56) References Cited

U.S. PATENT DOCUMENTS

| | | |
|---|---|---|
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Aarawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0206472 A1 | 7/2020 | Ma |
| 2020/0217733 A1 | 7/2020 | Lin |
| 2020/0222134 A1 | 7/2020 | Schuh |

FOREIGN PATENT DOCUMENTS

| | | |
|---|---|---|
| WO | WO 11/002215 | 1/2011 |
| WO | WO 12/082719 | 6/2012 |
| WO | WO 17/048194 | 3/2017 |
| WO | WO 17/053698 | 3/2017 |
| WO | WO 18/098477 | 5/2018 |

* cited by examiner

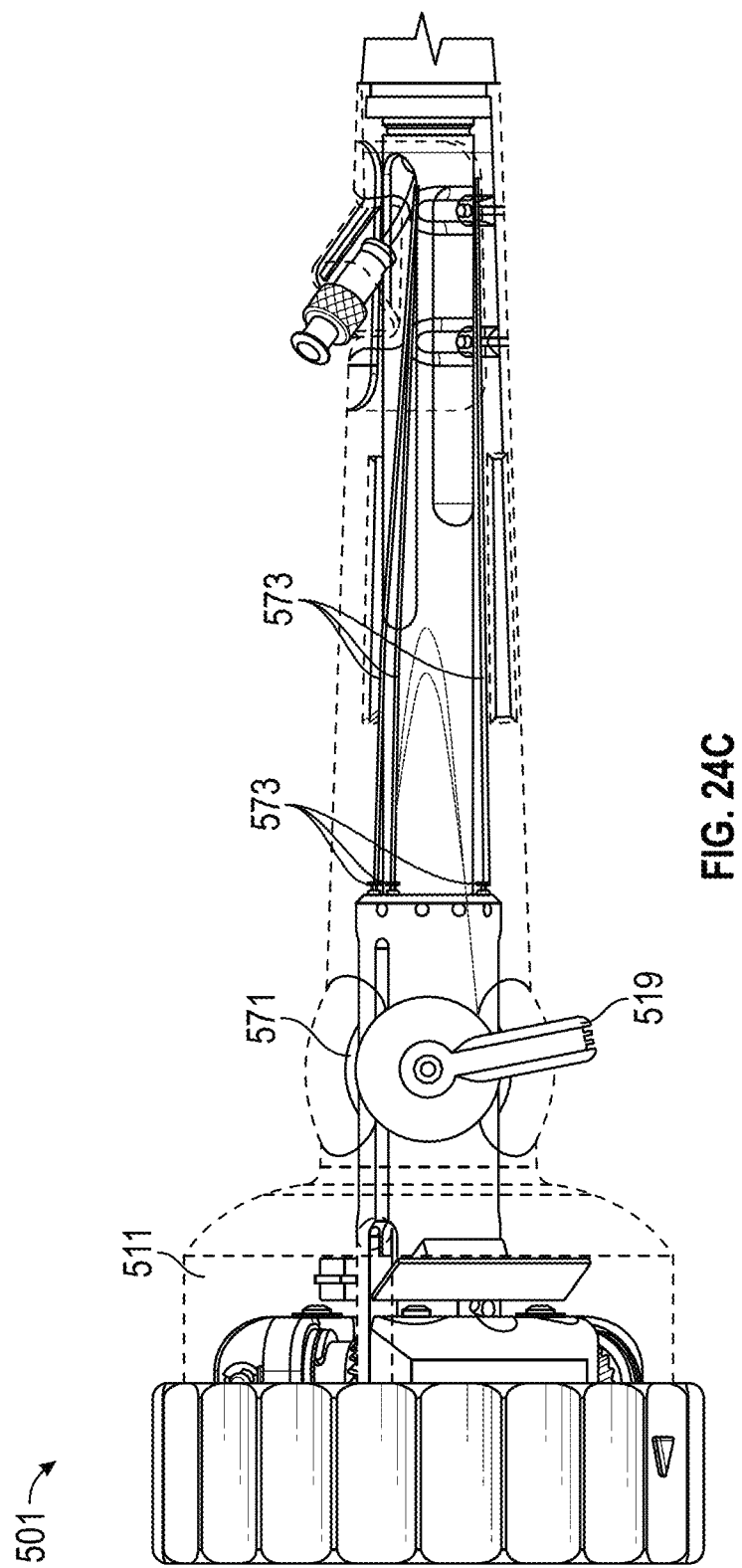

MANUALLY AND ROBOTICALLY CONTROLLABLE MEDICAL INSTRUMENTS

INCORPORATION BY REFERENCE TO ANY PRIORITY APPLICATIONS

This application claims priority to U.S. Provisional Application No. 62/722,665, filed Aug. 24, 2018, and U.S. Provisional Application No. 62/887,508, filed Aug. 15, 2019, each of which are incorporated herein by reference. Any and all applications for which a foreign or domestic priority claim is identified in the Application Data Sheet as filed with the present application are hereby incorporated by reference under 37 CFR 1.57.

TECHNICAL FIELD

The systems and methods disclosed herein are directed to medical instruments, and more particularly, to medical instruments that can be controllable both manually and robotically.

BACKGROUND

Medical procedures, such as endoscopy, may involve accessing and visualizing the inside of a patient's anatomy for diagnostic and/or therapeutic purposes. For example, gastroenterology, urology, and bronchology involve medical procedures that allow a physician to examine patient lumens, such as the ureter, gastrointestinal tract, and airways (bronchi and bronchioles). During these procedures, a thin, flexible tubular tool or instrument, known as an endoscope, is inserted into the patient through an orifice (such as a natural orifice) and advanced towards a tissue site identified for subsequent diagnosis and/or treatment. The medical instrument can be controllable and articulable to facilitate navigation through the anatomy.

SUMMARY

This application relates to manually and robotically controllable medical instruments that can be operated either manually or robotically. In some embodiments, in a first mode (a manual mode) a physician or other operator can physically handles and manually manipulates the medical instrument. In some embodiments, a second mode (a robotic mode) a robotically-enabled medical system can manipulate the medical instrument. When operated in the robotic mode, the medical instrument can be attached to an instrument drive mechanism that is positioned on the end of a robotic arm or other instrument positioning device.

In a first aspect, a medical instrument is described that includes an elongated shaft extending between a distal end and a proximal end and a first pull wire extending on or within the elongated shaft that is actuable to control articulation of the elongated shaft. The medical instrument also includes an instrument handle connected to the proximal end of the elongated shaft, the instrument handle configured to attach to an instrument drive mechanism. The instrument handle includes a first pulley assembly positioned within the instrument handle, wherein the first pull wire is positioned on the first pulley assembly such that rotation of the first pulley assembly actuates the first pull wire to cause articulation of the elongated shaft, a first manual drive input that is connected to the first pulley assembly such that manual actuation of the manual drive input causes rotation of the first pulley, a first robotic drive input. The first robotic drive input is configured to engage with a first robotic drive output of the instrument drive mechanism such that rotation of the first robotic drive output causes rotation of the first pulley assembly.

In some embodiments, the medical instrument can include one or more of the following features in any combination: (a) the medical instrument is configured to be manually controlled by manual actuation of the first manual drive input when the instrument handle is not attached to the instrument drive mechanism, and the medical instrument is configured to be robotically controlled by robotic actuation of the first robotic drive input when the instrument handle is attached to the instrument drive mechanism; (b) wherein the first manual drive input is separate from the first robotic drive input; (c) wherein the first manual drive input is manually accessible when the instrument handle is attached to the instrument drive mechanism; (d) wherein the first manual drive input is configured to provide manual two-way deflection control of the elongated shaft, and the first robotic drive input is configured to provide four-way deflection control of the elongated shaft; (e) wherein the first pull wire is actuable to control articulation of the elongated shaft in a first articulation direction, the first pull wire is wound on the first pulley assembly in a first winding direction, and the medical instrument further comprises a second pull wire extending on or within the elongated shaft, the second pull wire actuable to control articulation of the elongated shaft in a second articulation direction opposite the first articulation direction, wherein the second pull wire is wound on the first pulley assembly in a second winding direction opposite the first winding direction; (f) wherein the first pulley assembly comprises a first pulley shaft positioned within the base, a first pulley positioned on the first pulley shaft, the first pull wire wound on the first pulley, and second pulley positioned on the first pulley shaft, the second pull wire wound on the second pulley; (g) wherein at least one of the first pulley and the second pulley are keyed with respect to the first pulley shaft such that the at least one of the first pulley and the second pulley can be mounted on the first pulley shaft at any of a plurality of different rotational positions with respect to the first pulley shaft; (h) a third pull wire extending on or within the elongated shaft, the third pull wire actuable to control articulation of the elongated shaft in a third articulation direction, a fourth pull wire extending on or within the elongated shaft, the fourth pull wire actuable to control articulation of the elongated shaft in a fourth articulation direction opposite the third articulation direction, and a second robotic drive input configured to engage with a second robotic drive output of the instrument drive mechanism such that the rotation of the second robotic drive output causes rotation of the second pulley assembly to control articulation of the elongated shaft in the third and fourth; (i) wherein the first manual drive input is directly coupled to the first pulley assembly; (j) wherein the first manual drive input is coupled to the first pulley assembly by a geared assembly; (k) a manual roll input configured to provide manual roll control of the elongated shaft; (l) a robotic roll input configured to provide robotic roll control of the elongated shaft; (m) wherein the first pull wire extends within a first coil pipe within the elongated shaft; (n) wherein the first pull wires and the first coil pipe include service loops to permit roll of the elongated shaft; (o) wherein the service loops permit roll of the elongated shaft in both rotational directions of at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, or at least 360 degrees; (p) wherein the first pull wire includes an increased diameter in a region wound on the first pulley assembly; (q) wherein the first manual drive input disengages when the instrument handle is attached to the instrument drive mechanism; (r) wherein the first manual drive inputs comprises at least one of a lever, a wheel, and a slider; (s) wherein the instrument handle is configured to cover only some of the drive outputs on the instrument drive mechanism when the instrument handle is attached to the instrument drive mechanism; and/or (t) wherein the first manual drive input comprises a pivot-based movement and the first robotic drive input comprises a rotational movement.

In another aspect, a medical instrument is described that includes an elongated shaft extending between a distal end and a proximal end, a first pull wire extending on or within the elongated shaft, the first pull wire actuable to control articulation of the elongated shaft, and an instrument handle connected to the proximal end of the elongated shaft, the instrument handle configured to attach to an instrument drive mechanism. The instrument handle includes a first pulley assembly positioned within the instrument handle, wherein the first pull wire is positioned on the first pulley assembly, a first robotic drive input, the first robotic drive input configured to engage with a first robotic drive output of the instrument drive mechanism such that the rotation of the first robotic drive output causes rotation of the first pulley assembly, a manual deflection pulley disposed between the first pulley assembly and the distal end of the elongated shaft, wherein the first pull wire is wound on the manual deflection pulley, and a first manual drive input configured to be actuated manually that is connected to the manual deflection pulley such that actuation of the manual drive input causes rotation of the first pulley.

In another aspect, a medical instrument is described that includes an elongated shaft extending between a distal end and a proximal end, a first pull wire extending on or within the elongated shaft, the first pull wire actuable to control articulation of the elongated shaft, and an instrument handle connected to the proximal end of the elongated shaft, the instrument handle configured to attach to an instrument drive mechanism. The instrument handle can include a first pulley assembly positioned within the instrument handle, wherein the first pull wire is positioned on the first pulley assembly such that rotation of the first pulley assembly actuates the first pull wire to cause articulation of the elongated shaft, a first manual drive input configured to be actuated manually that is connected to the first pulley assembly such that actuation of the manual drive input causes rotation of the first pulley, a first robotic drive input that is connected to the first pulley assembly, the first robotic drive input configured to engage with a first robotic drive output of the instrument drive mechanism such that the rotation of the first robotic drive output causes rotation of the first pulley assembly, a second robotic drive input coupled to a shaft roll pulley, and a coupler gear on the elongated shaft engaged with the shaft roll pulley such that rotation of the second robotic drive input causes roll of the elongated shaft. In some embodiments, the elongated shaft is configured to be manually rollable relative to the instrument handle.

In another aspect, a method for controlling a medical instrument includes manually actuating a manual drive input on an instrument handle of the medical instrument to actuate a pulley assembly within the medical instrument to control articulation of an elongated shaft of the medical instrument; attaching the instrument handle to an instrument drive mechanism; and robotically actuating a robotic drive input on the instrument handle with the instrument drive mechanism to cause articulation of the pulley assembly to control articulation of the elongated shaft of the medical instrument.

In some embodiments, the medical instrument can include one or more of the following features in any combination: (a) manually actuating the manual drive input comprises manually manipulating the manual drive input to provide two-way deflection control of the elongated shaft of the medical instrument, and robotically actuating the robotic drive input comprises robotically manipulating the robotic drive input to provide four-way deflection control of the elongated shaft of the medical instrument; (b) wherein robotically actuating the robotic drive input further comprises robotically manipulating the robotic drive input to provide roll control of the elongated shaft of the medical instrument; (c) wherein manually actuating the robotic drive input further comprises manually rotating the elongated shaft with respect to the handle to provide roll control for the elongated shaft; (d) wherein the manual drive input comprises a lever, a wheel, or a slider; and/or (e) wherein the robotic drive input comprises at least three robotic drive inputs configured to engage with at least three robotic drive outputs on the instrument drive mechanism.

In another aspect, a robotic medical system includes a first medical instrument comprising a first instrument base and an elongated shaft extending from the instrument base, the instrument base includes at least one first robotic drive input. The system also includes a second medical instrument comprising a second instrument base and at least one second robotic drive input. The system also includes an instrument drive mechanism engaged with first instrument base of the first medical instrument and the second instrument base of the second medical instrument. The instrument drive mechanism comprises at least one first robotic drive output engaged with and configured to drive the at least one first robotic drive input of the first medical instrument, and at least one second robotic drive output engaged with and configured to drive the at least one second robotic drive input of the second medical instrument.

In some embodiments, the system can include one or more of the following features in any combination: (a) wherein the instrument drive mechanism is positioned on a robotic arm; (b) wherein the robotic arm is configured to move the instrument drive mechanism to reposition the first medical instrument and the second medical instrument simultaneously; (c) wherein the first instrument base comprises a cutout configured to expose the at least one second drive input when the first instrument base is engaged with the instrument drive mechanism, and the second instrument base is at least partially received within the cutout; (d) wherein the at least one first robotic drive input comprises three first robotic drive inputs, and the at least one second robotic drive input comprises two second robotic drive inputs; (e) wherein the first medical instrument and the second medical instrument are arranged side-by-side when engaged with the instrument drive mechanism; (f) wherein the at least one first robotic drive output drives the at least one first robotic drive input to articulate the elongated shaft of the first medical instrument; (g) wherein the at least one second robotic drive output drives the at least one second robotic drive input to actuate a function of the second medical instrument; (h) wherein the instrument drive mechanism is configured to actuate the first medical instrument and the second medical instrument simultaneously; and/or (i)

wherein the first medical instrument further comprises a first manual drive input configured to allow manual control of the first medical instrument.

In another aspect, a method is disclosed that includes attaching a first instrument base of a first medical instrument to an instrument drive mechanism positioned on a first robotic arm such that a first robotic drive output of the instrument drive mechanism engages a first robotic drive input of the first instrument base; attaching a second instrument base of a second medical instrument to the instrument drive mechanism positioned on the first robotic arm such that a second robotic drive output of the instrument drive mechanism engages a second robotic drive input of the second instrument base; actuating the first medical instrument by driving the first robotic drive input with the first robotic drive output; and actuating the second medical instrument by driving the second robotic drive input with the second robotic drive output.

In some embodiments, the method includes one or more of the following features in any combination: (a) wherein attaching the first instrument base to the instrument drive mechanism comprises attaching the first instrument base to the instrument drive mechanism such that the second robotic drive input remains exposed; (b) manually actuating a first manual drive input of the first medical instrument to manually control the first medical instrument; (c) wherein the first medical instrument comprises an elongated shaft extending from the instrument base, and the first manual drive input is configured to drive two-way deflection of the elongated shaft; (d) wherein manually actuating the first manual drive input of the first medical instrument occurs prior to attaching the first instrument base to the instrument drive mechanism; (e) moving the first robotic arm to move the first medical instrument and the second medical instrument; (f) wherein the first medical instrument comprises an elongated shaft extending from the instrument base, and the instrument drive mechanism is configured to drive four-way deflection of the elongated shaft; and/or (g) wherein the first instrument base and the second instrument base are arranged side by side on the instrument drive mechanism.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 21A illustrates a perspective view of the medical instrument, which includes an instrument handle and an elongated shaft.

FIG. 21B illustrates a first side view of the instrument handle of the medical instrument of FIG. 21A.

FIG. 21C illustrates a second side view of the instrument handle of the medical instrument of FIG. 21A.

FIG. 21D illustrates a first side view of some of the internal components of the instrument handle of the medical instrument of FIG. 21A.

FIG. 21E illustrates an embodiment of a pulley assembly of the instrument handle of the medical instrument of FIG. 21A.

FIG. 21F illustrates connection of a manual drive input to the pulley system of FIG. 21E according to one embodiment.

FIG. 22A is a perspective view of the instrument handle attached to the instrument drive mechanism.

FIG. 22B is a top view of the instrument handle attached to the instrument drive mechanism.

FIG. 22C is a side view of the instrument handle attached to the instrument drive mechanism.

FIG. 23A illustrates a perspective view of the medical instrument, which includes an instrument handle and an elongated shaft.

FIG. 23B illustrates a first side view of the instrument handle of the medical instrument of FIG. 23A.

FIG. 23C illustrates a partial second side view of the instrument handle of the medical instrument of FIG. 23A.

FIG. 23D illustrates a first side view of some of the internal components of the instrument handle of the medical instrument of FIG. 23A.

FIG. 23E illustrates a perspective view of some of the internal components of the instrument handle of the medical instrument of FIG. 23A.

FIG. 23F illustrates an embodiment of a pulley assembly of the instrument handle of the medical instrument of FIG. 23A.

FIG. 23G illustrates a first side view of an embodiment of a manual drive input for the medical instrument of FIG. 23A.

FIG. 23H illustrates a cross-sectional view of the instrument handle of the medical instrument of FIG. 23A showing connection of the manual drive input to the pulley assembly according to one embodiment.

FIGS. 24A-24E illustrate various views of another embodiment of a manually and robotically controllable medical instrument.

FIG. 24A illustrates a perspective view of the medical instrument, which includes an instrument handle and an elongated shaft.

FIG. 24B illustrates a perspective view of the instrument handle of the medical instrument of FIG. 24A.

FIG. 24C illustrates a side view of the instrument handle of the medical instrument of FIG. 24A.

FIG. 24D illustrates a perspective view of the instrument handle of the medical instrument of FIG. 24A and shows an embodiment of a manual drive input according to one embodiment.

FIG. 24E illustrates a perspective cross-sectional view of some of the internal components of the instrument handle of the medical instrument of FIG. 24A.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
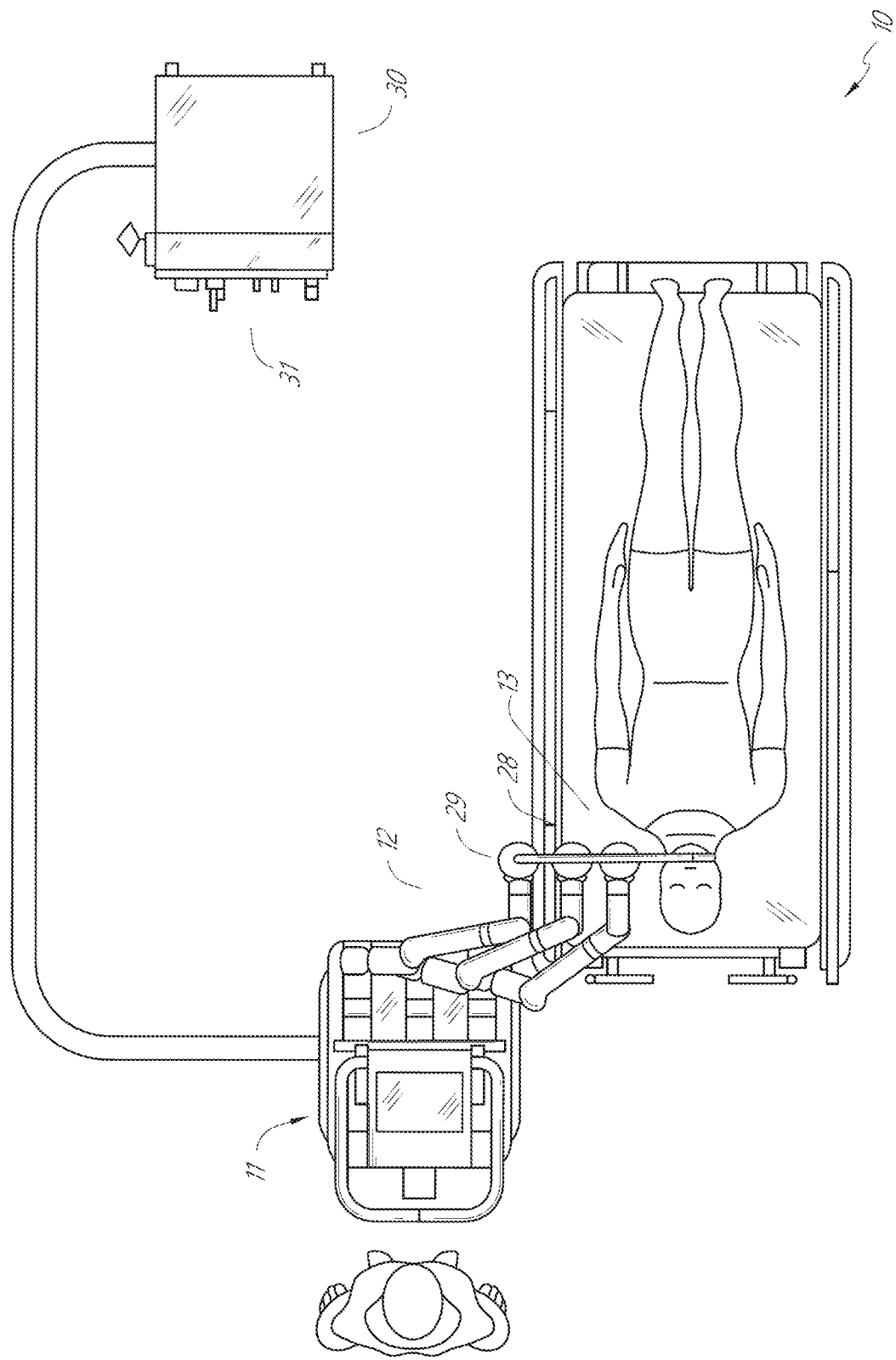
FIG. 1 illustrates an embodiment of a cart-based robotic system arranged for diagnostic and/or therapeutic bronchoscopy.
Figure 2:
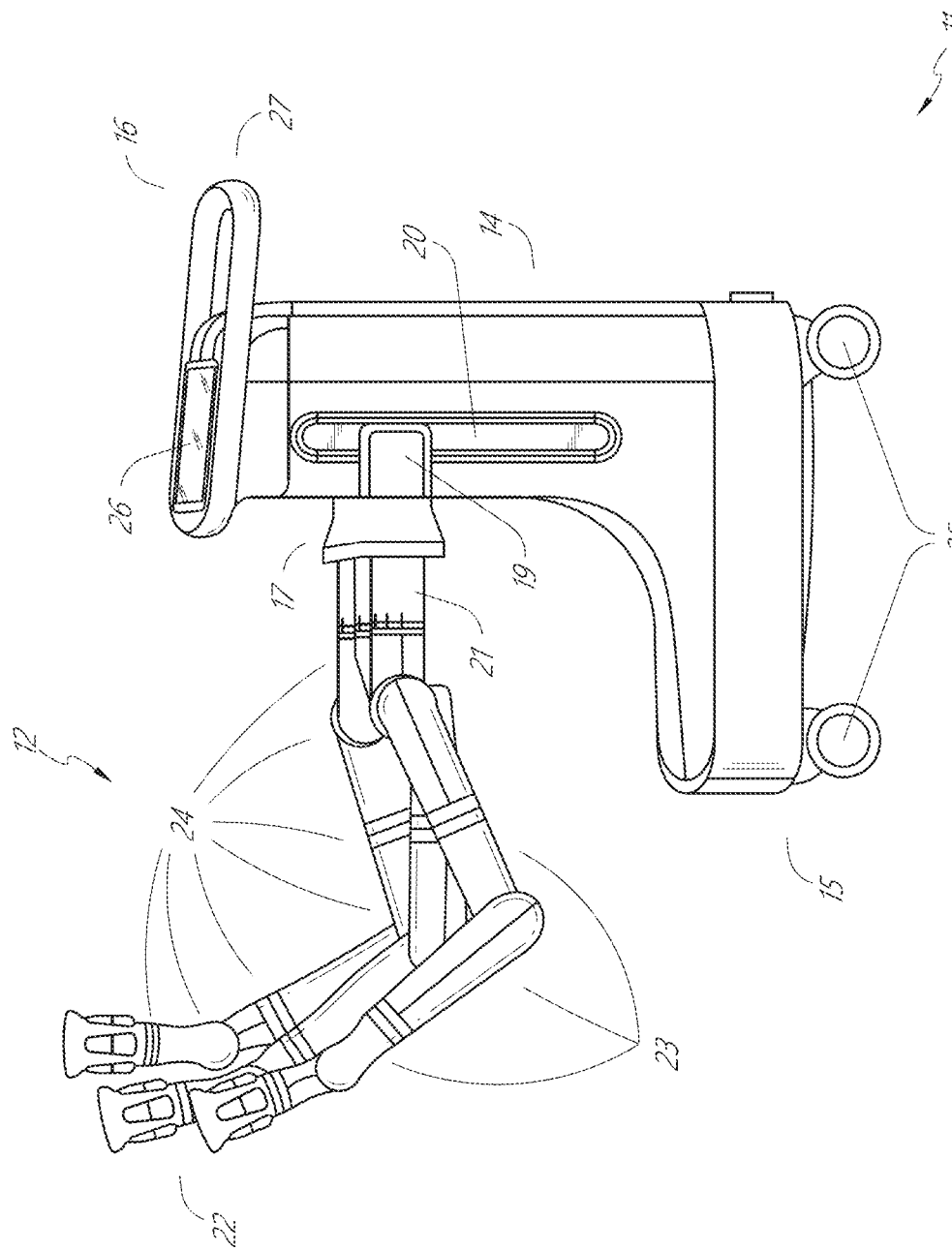
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
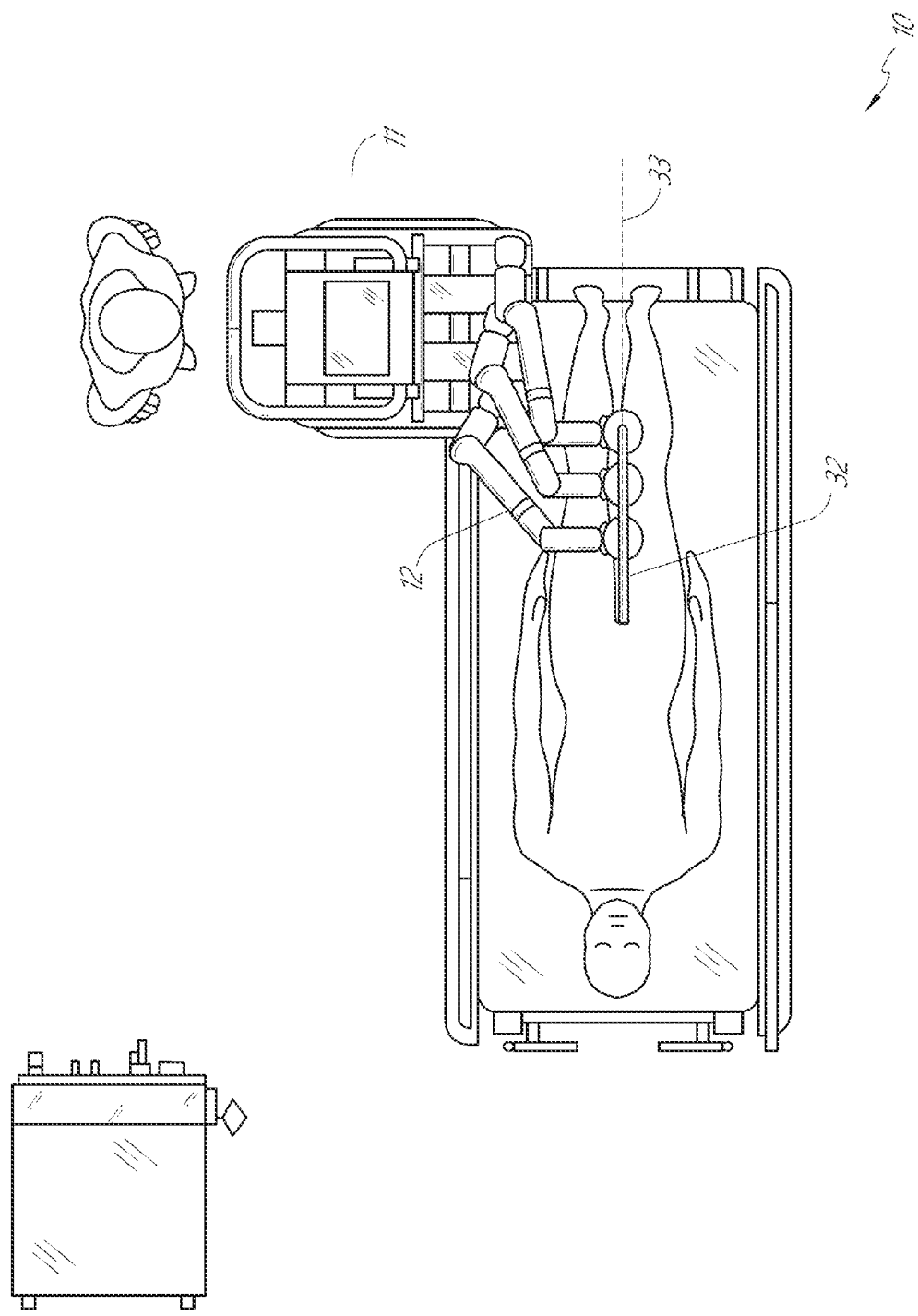
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
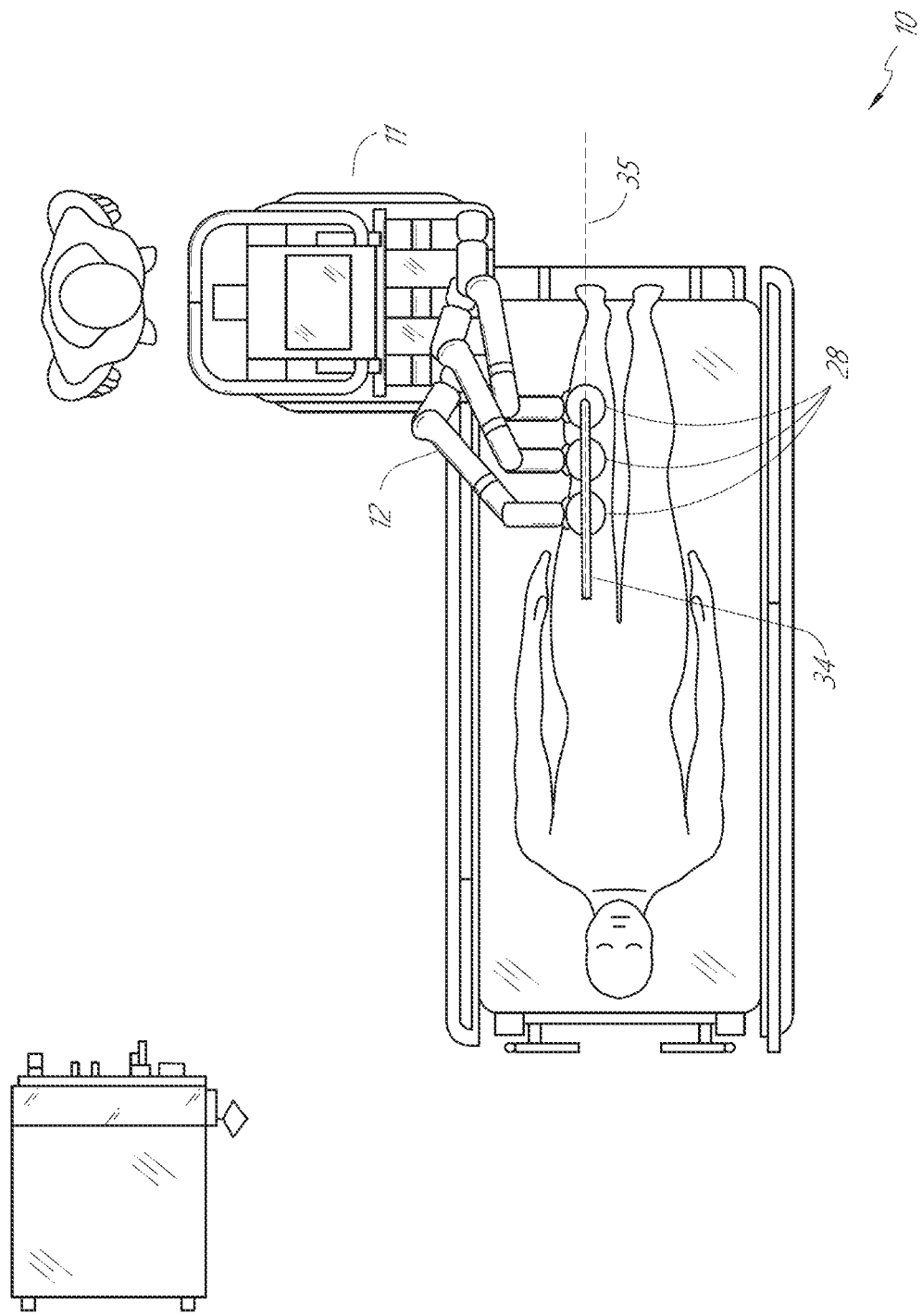
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
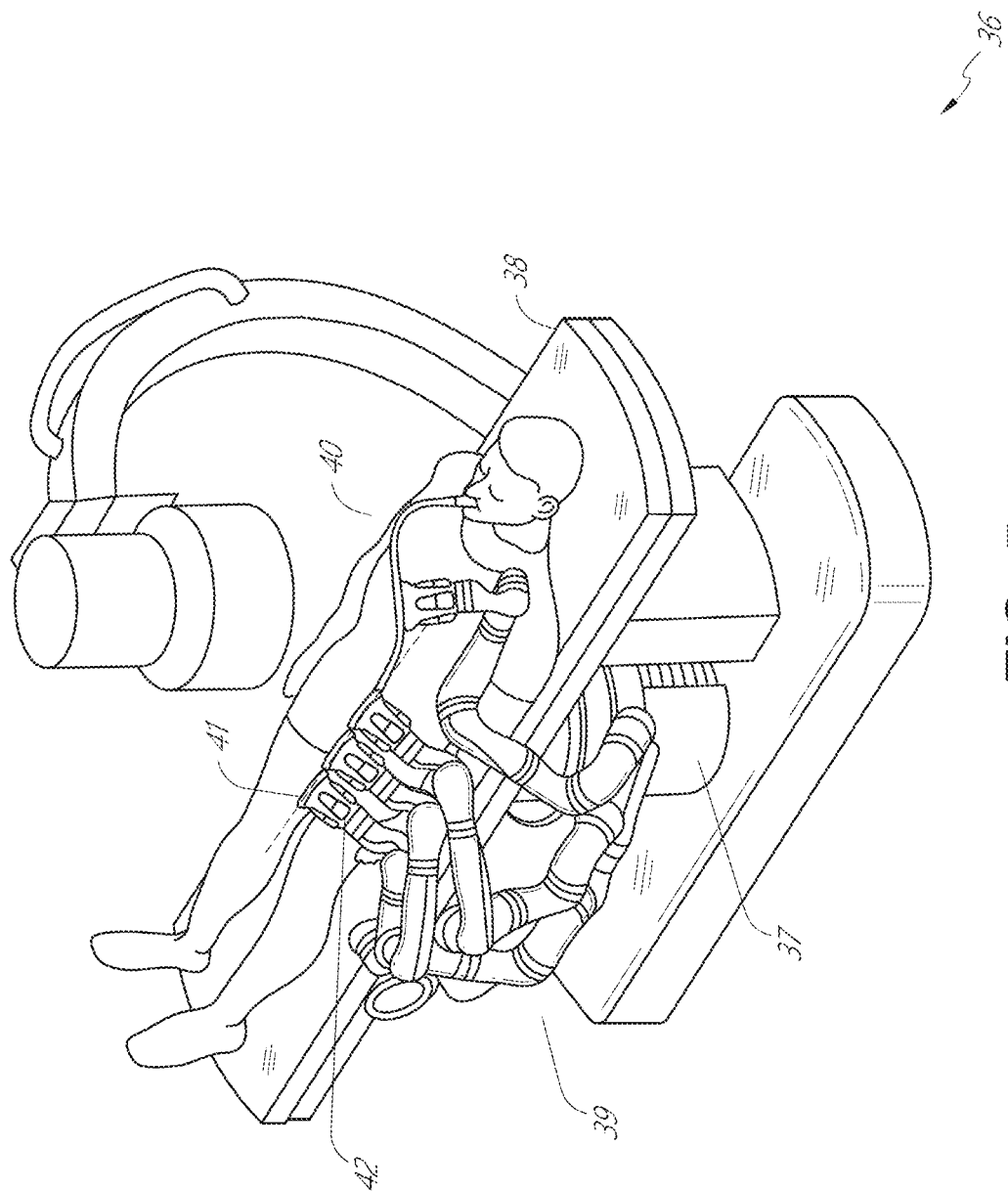
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
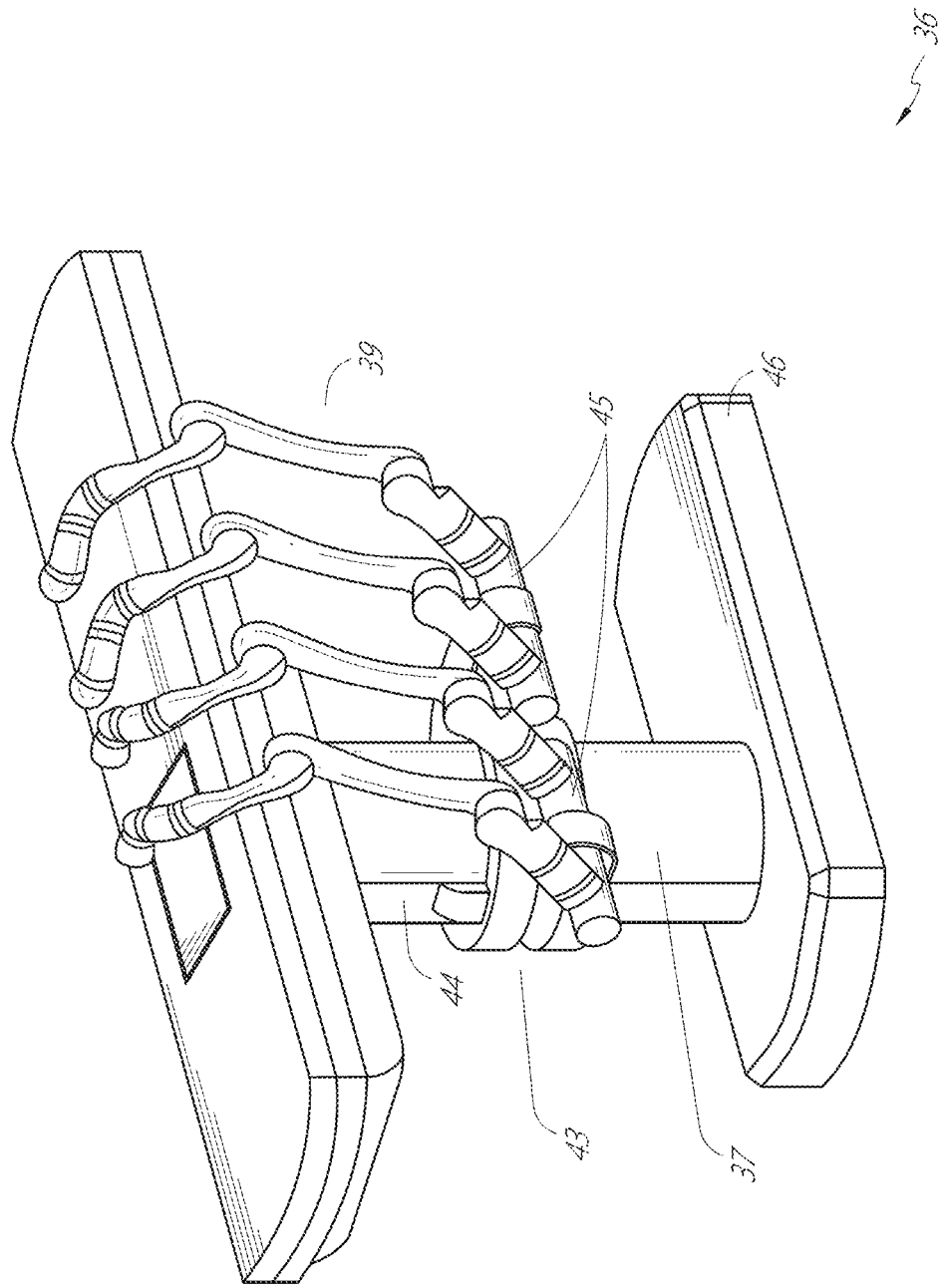
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
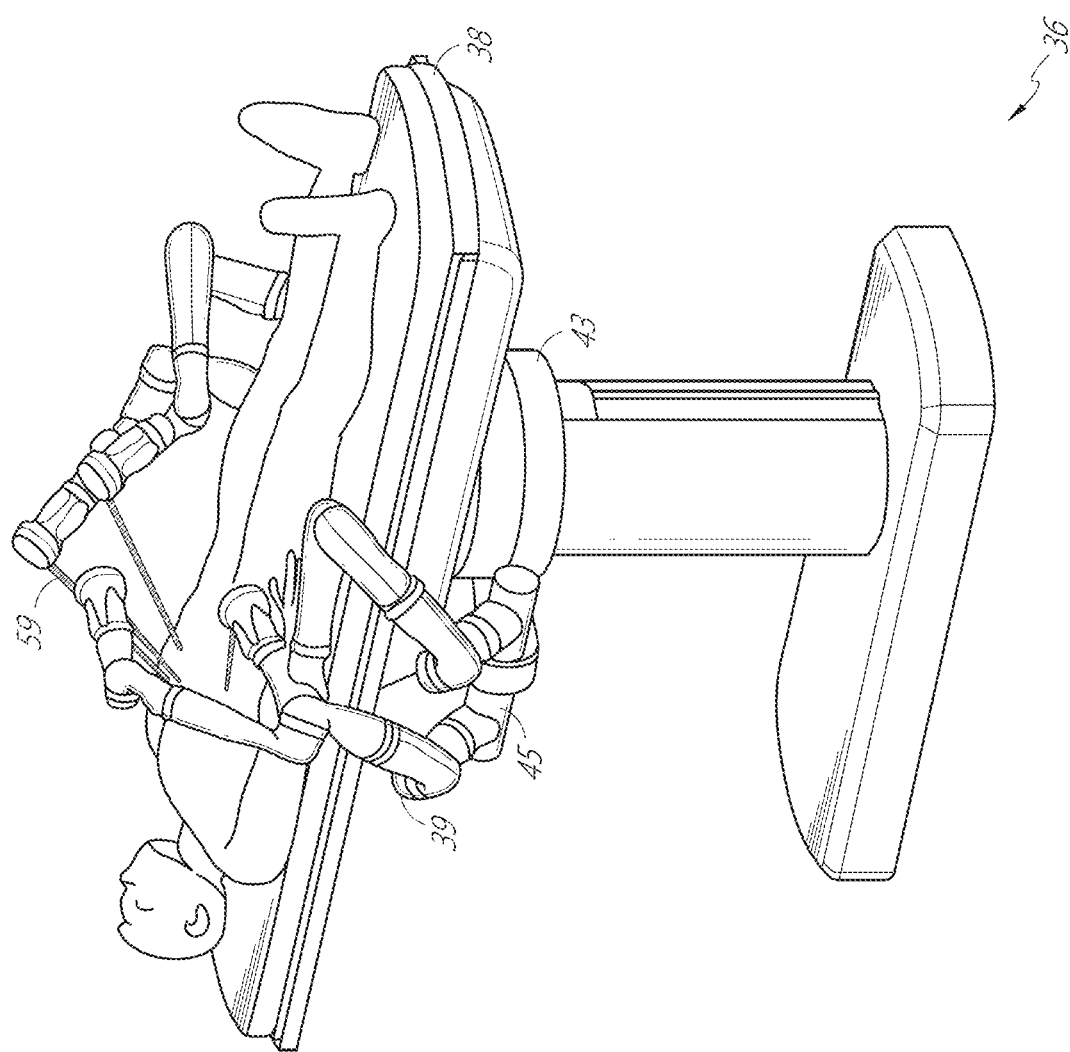
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
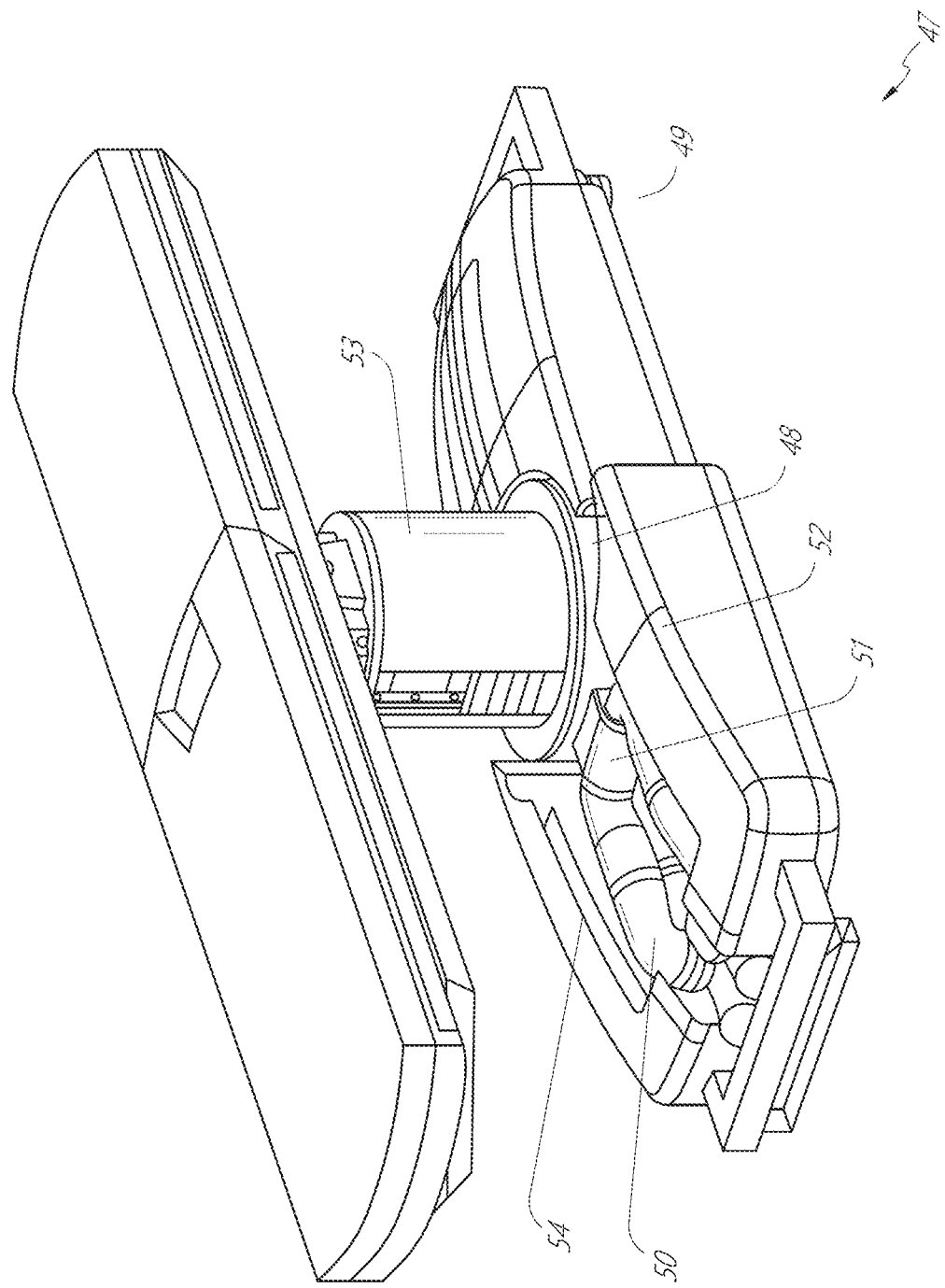
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
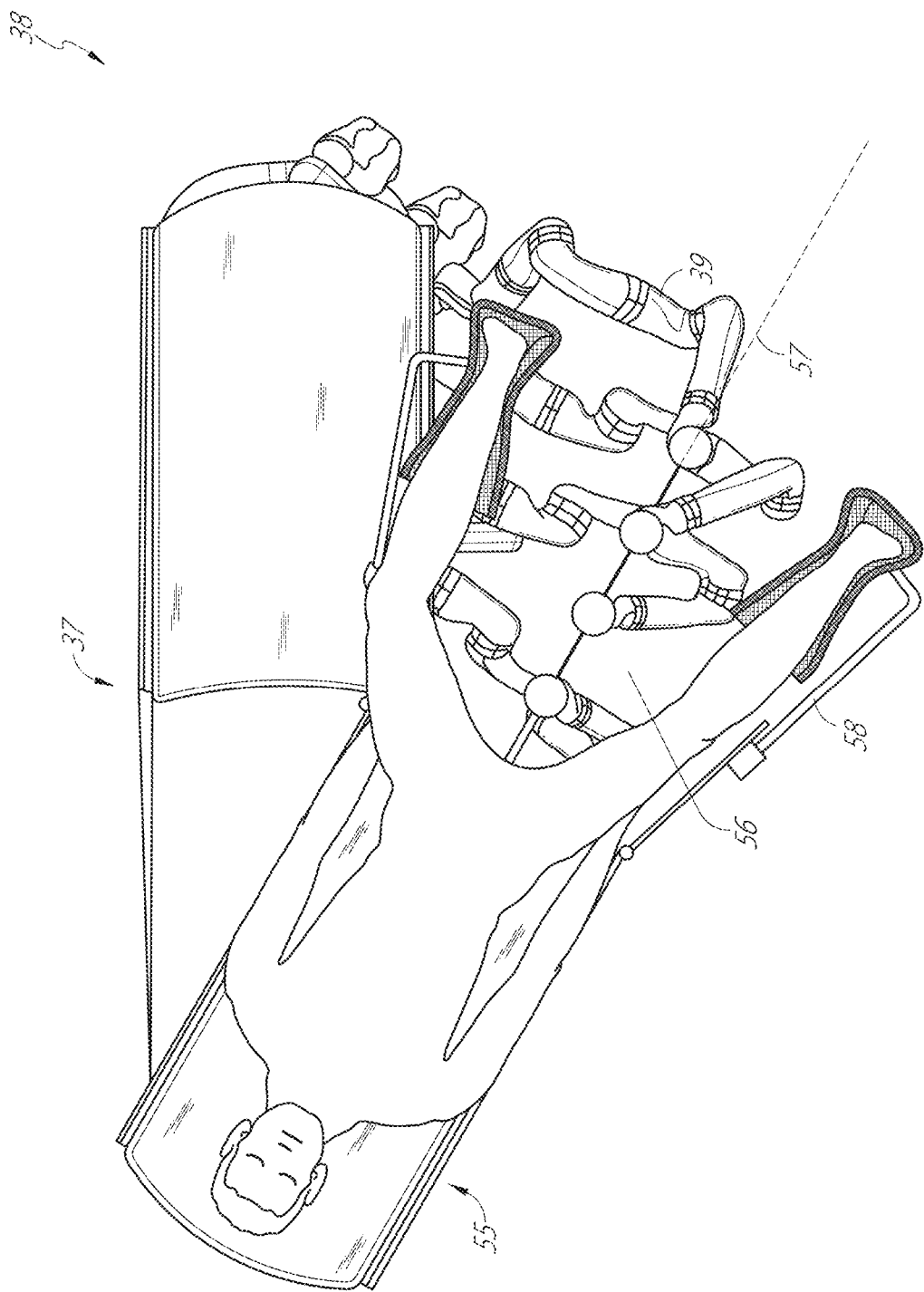
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
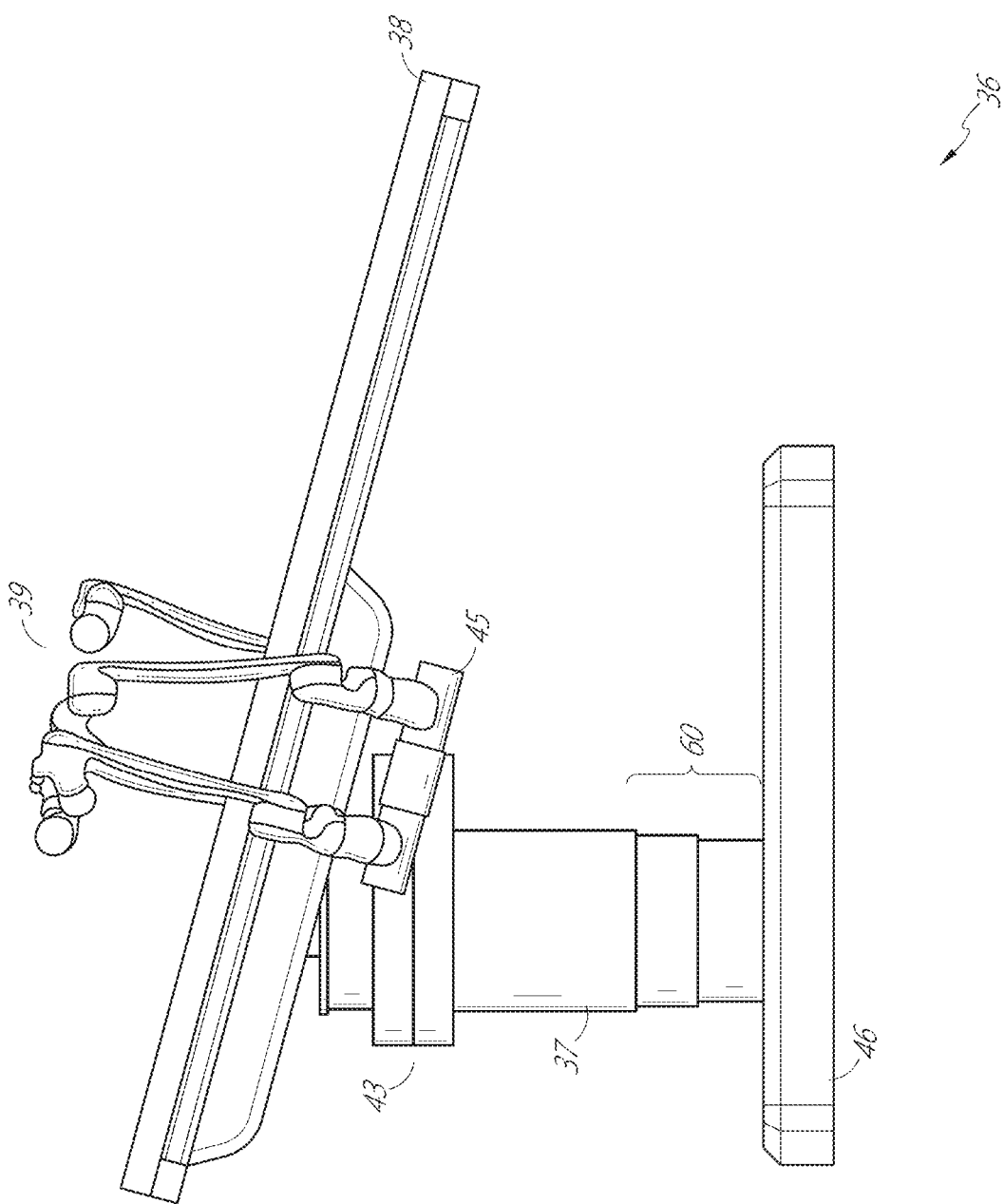
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
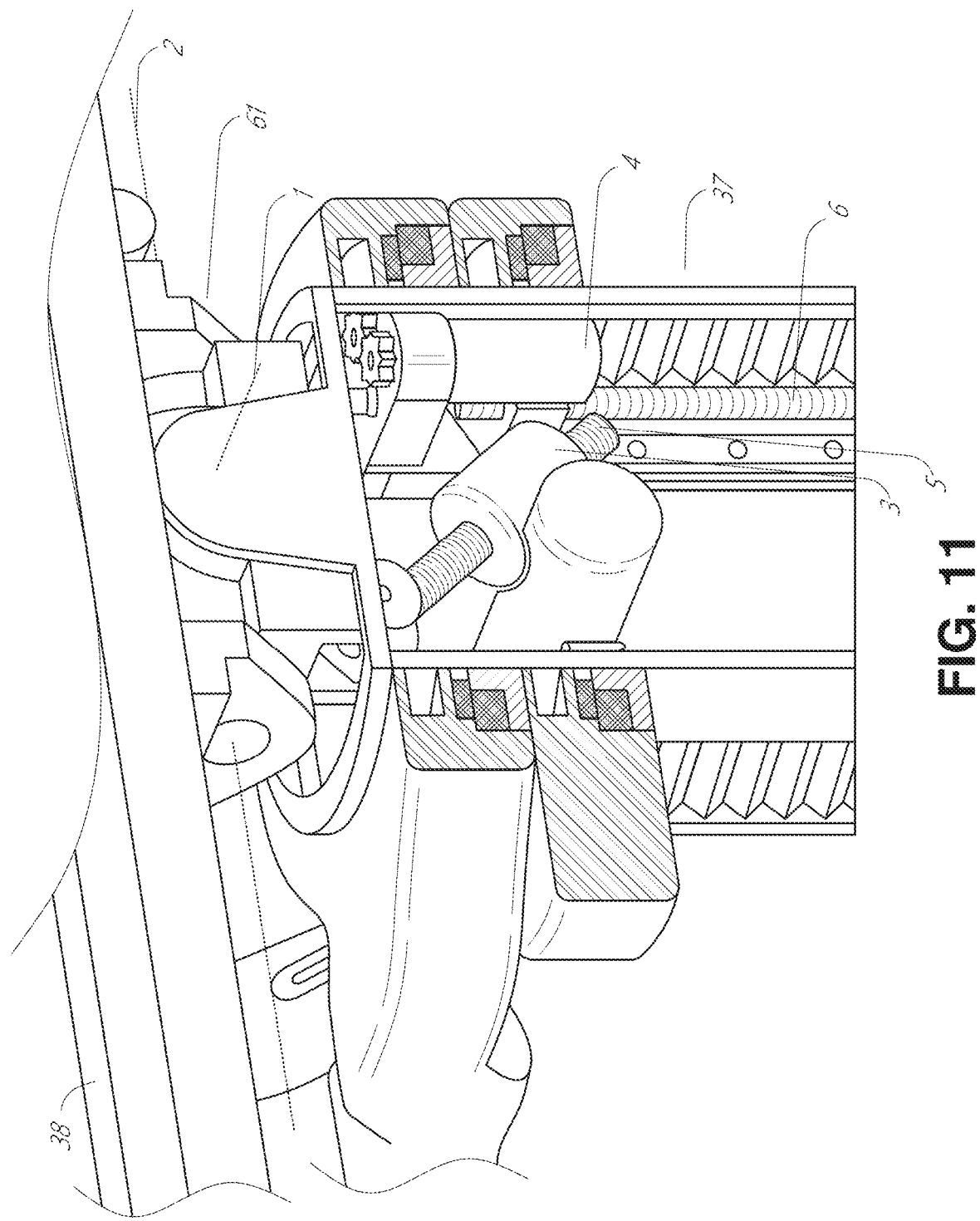
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
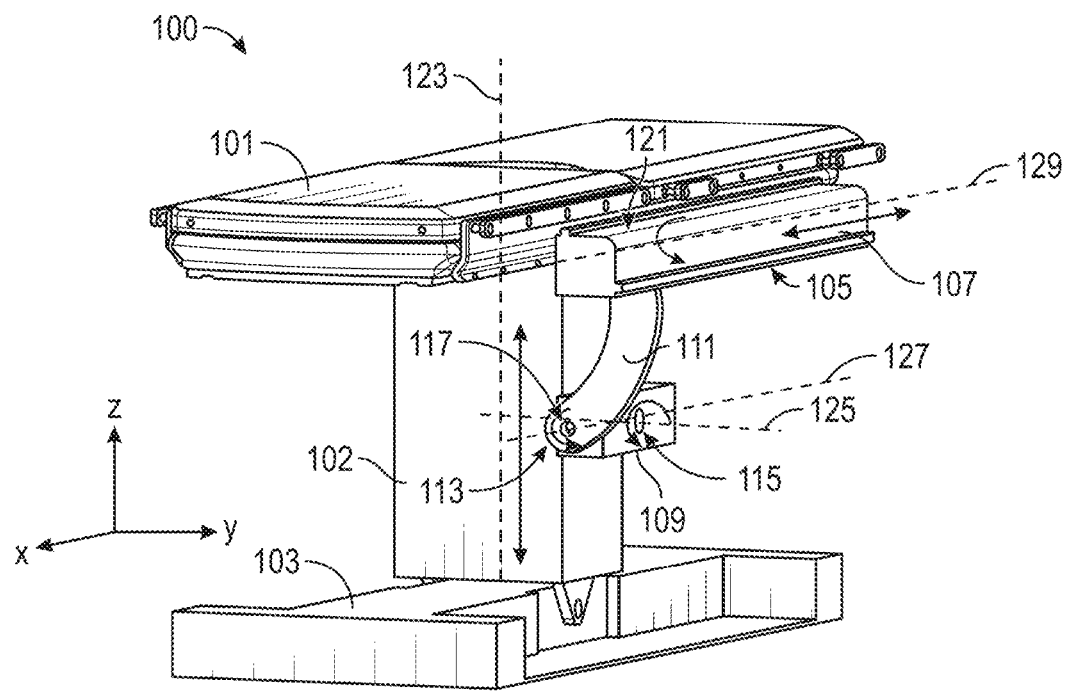
FIG. 12 illustrates an alternative embodiment of a table-based robotic system.
Figure 13:
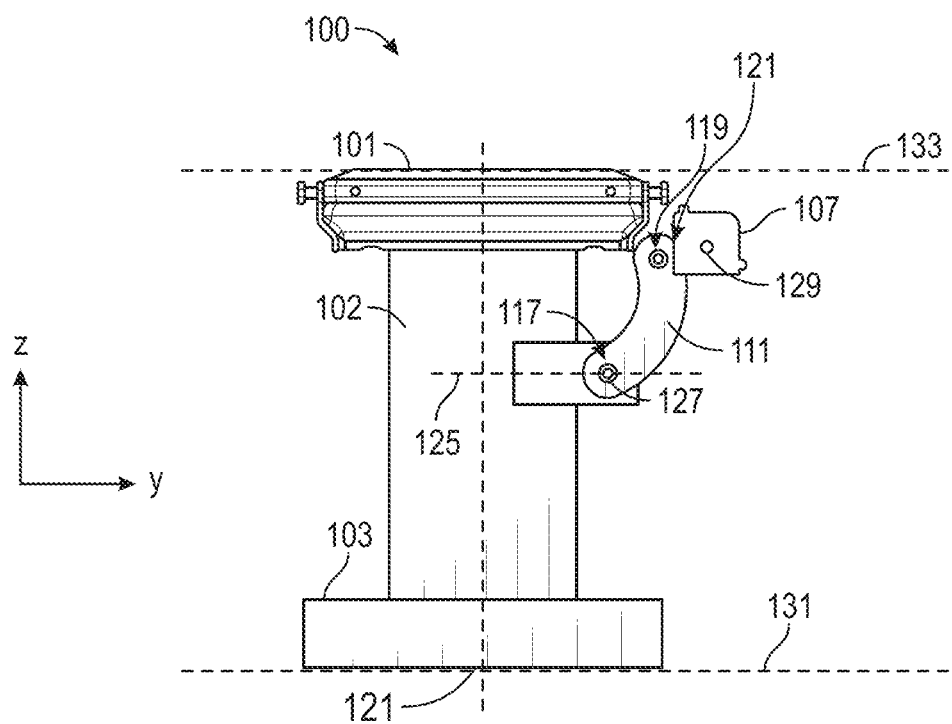
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
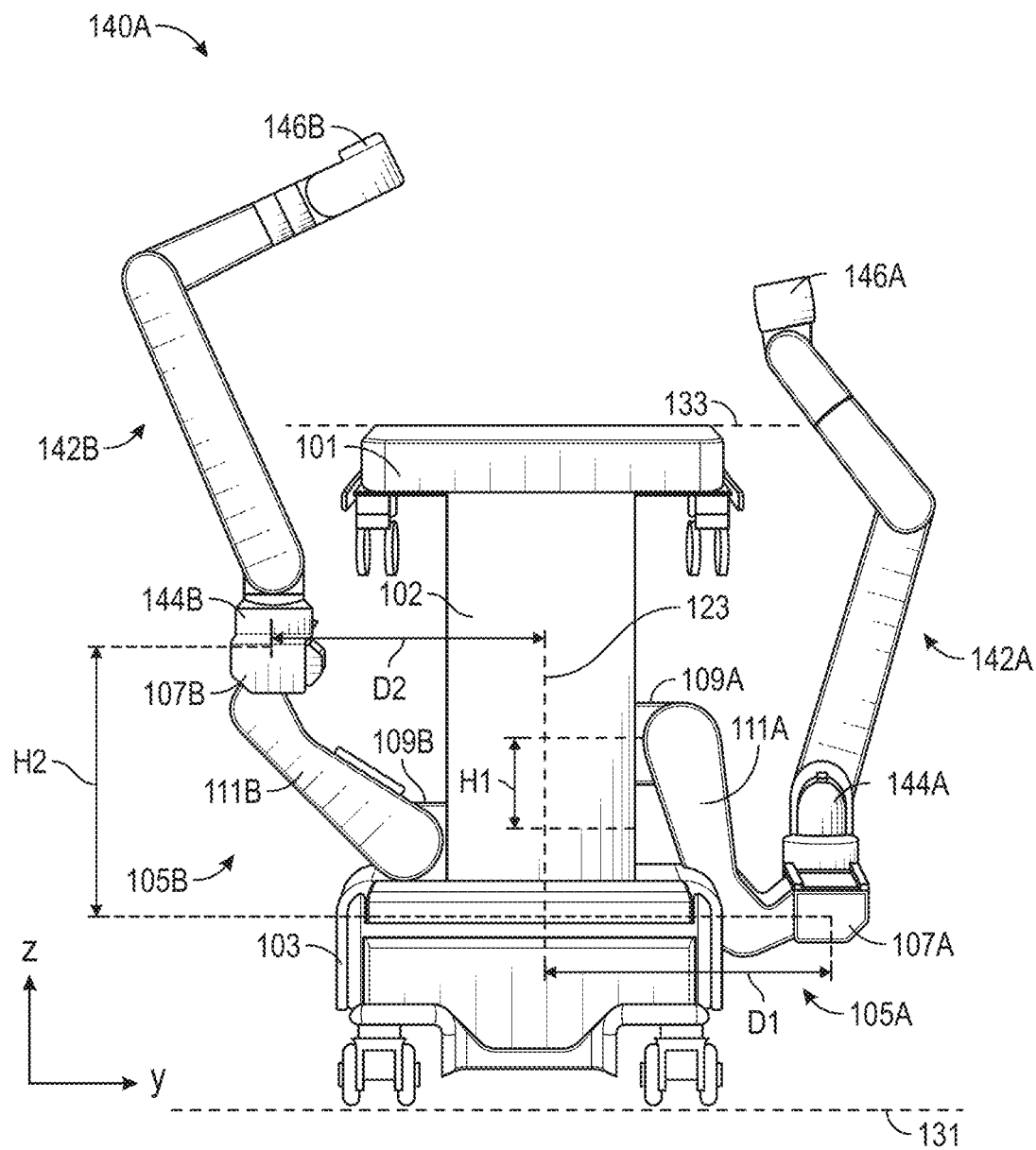
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
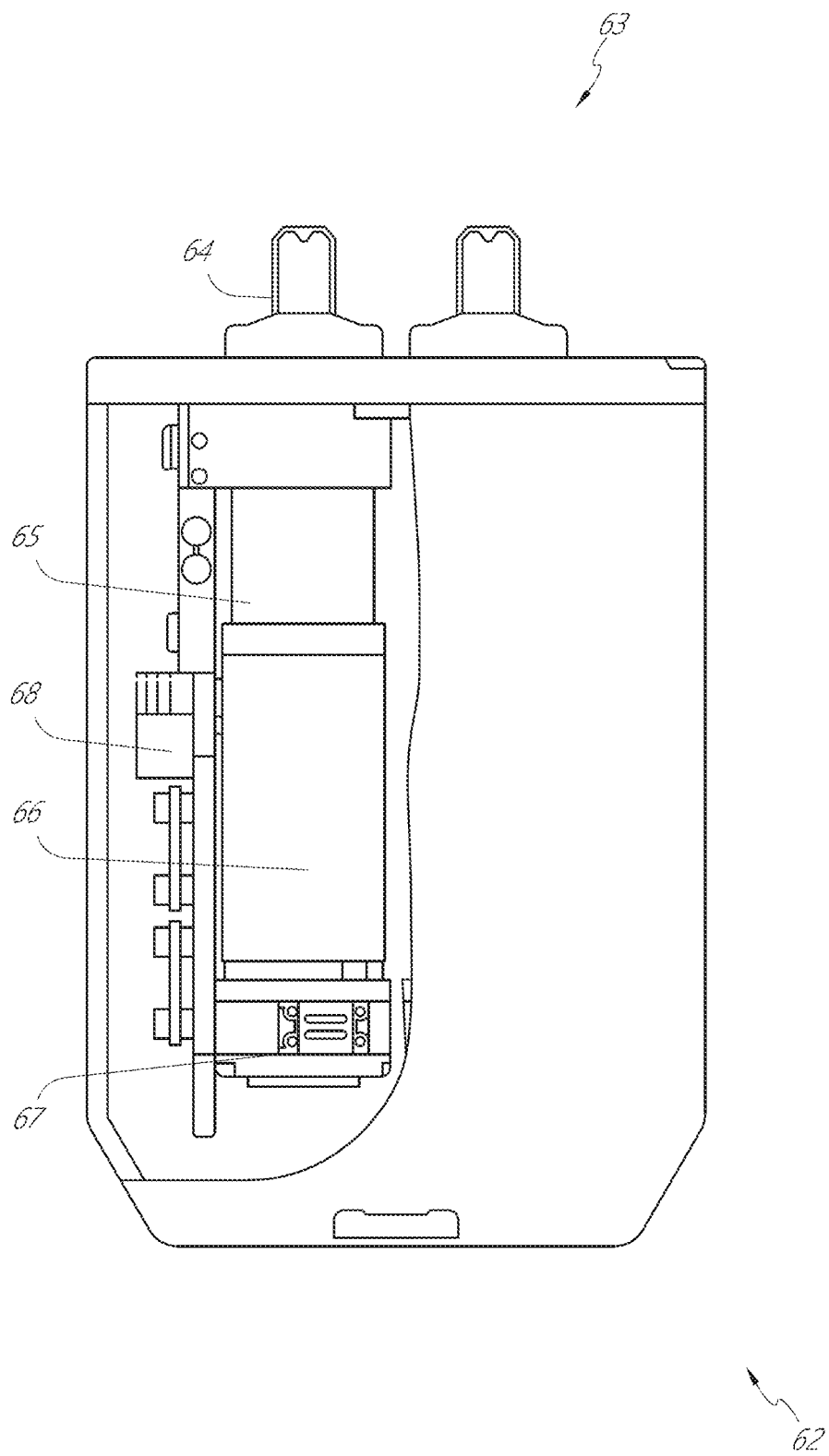
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
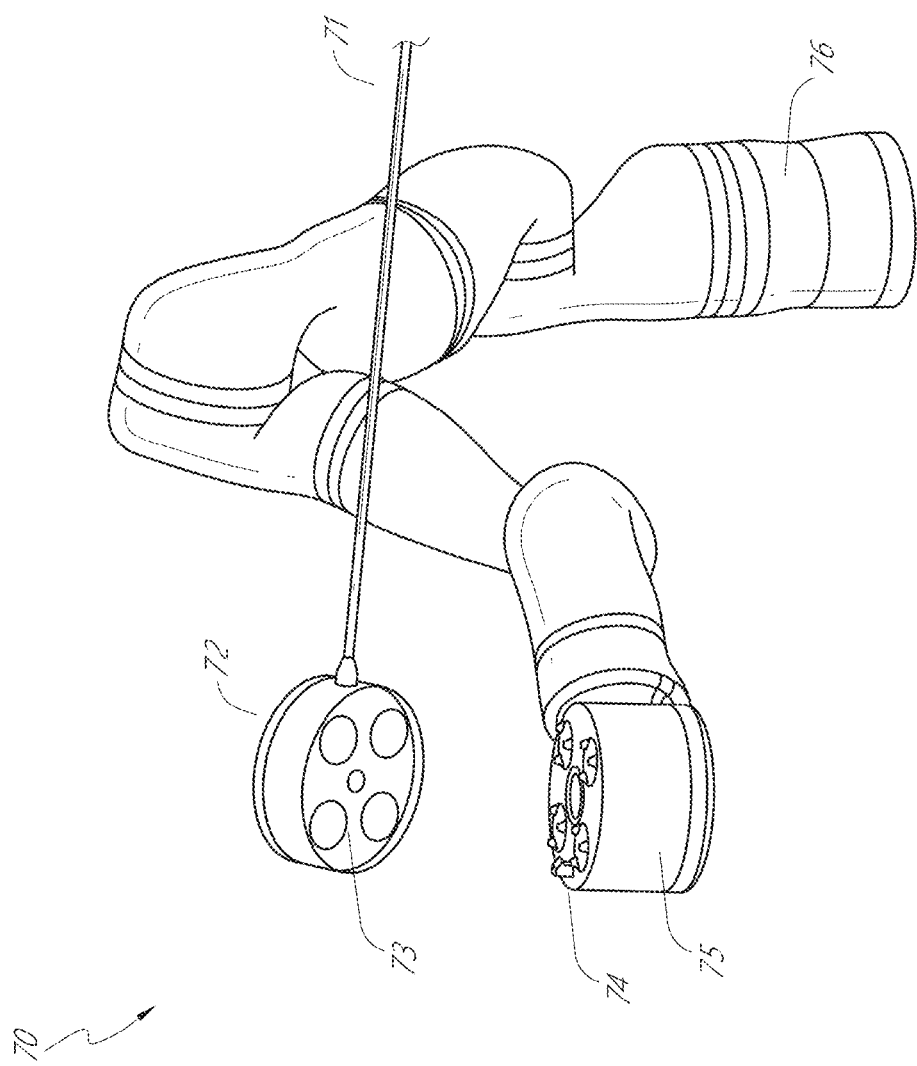
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
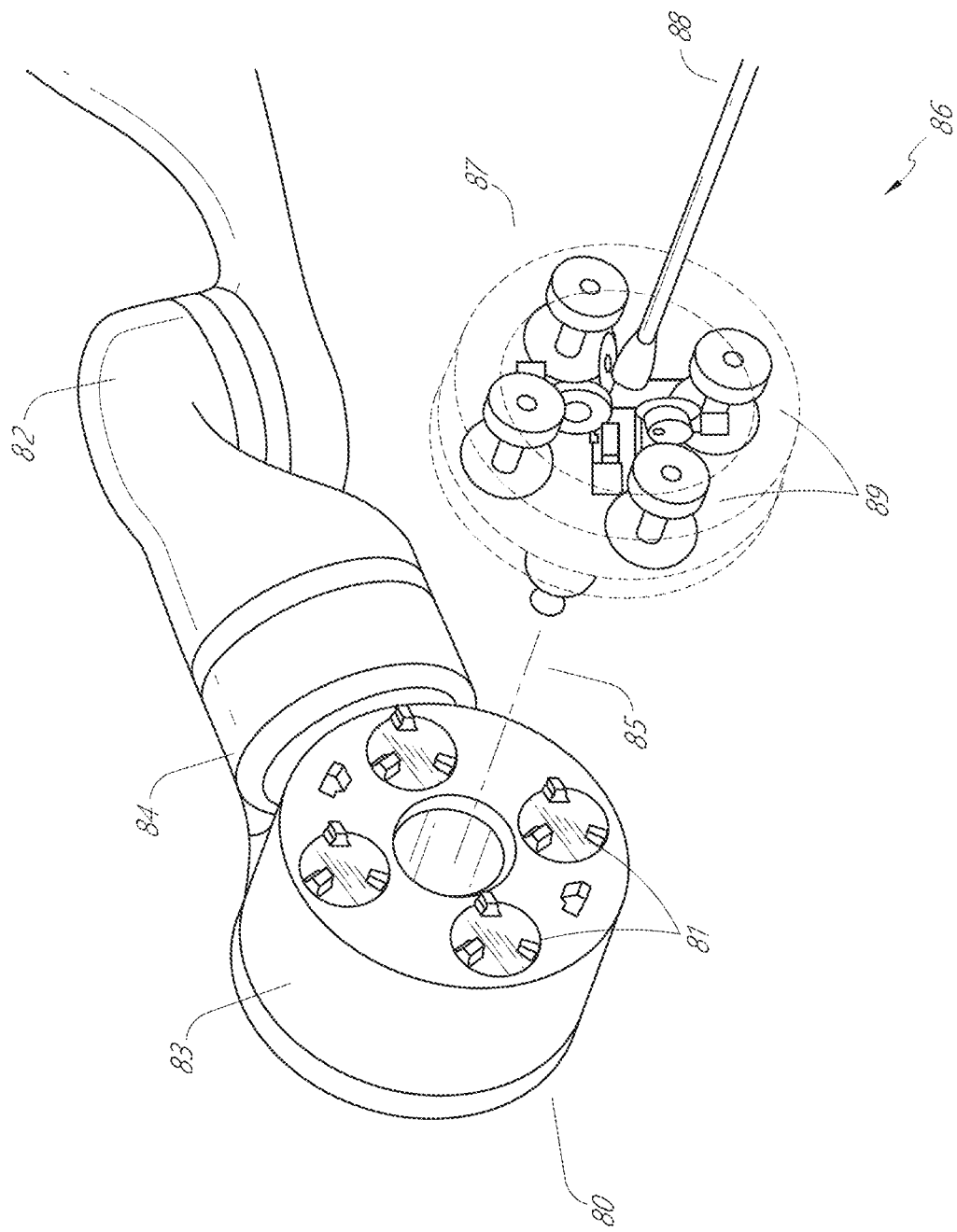
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
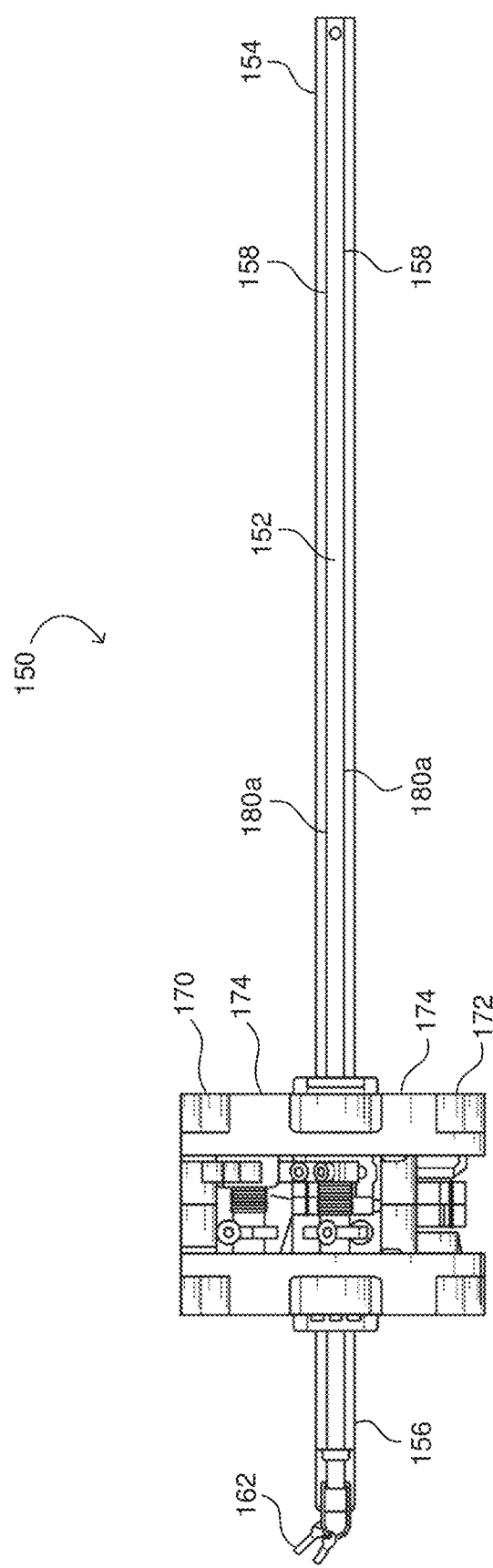
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
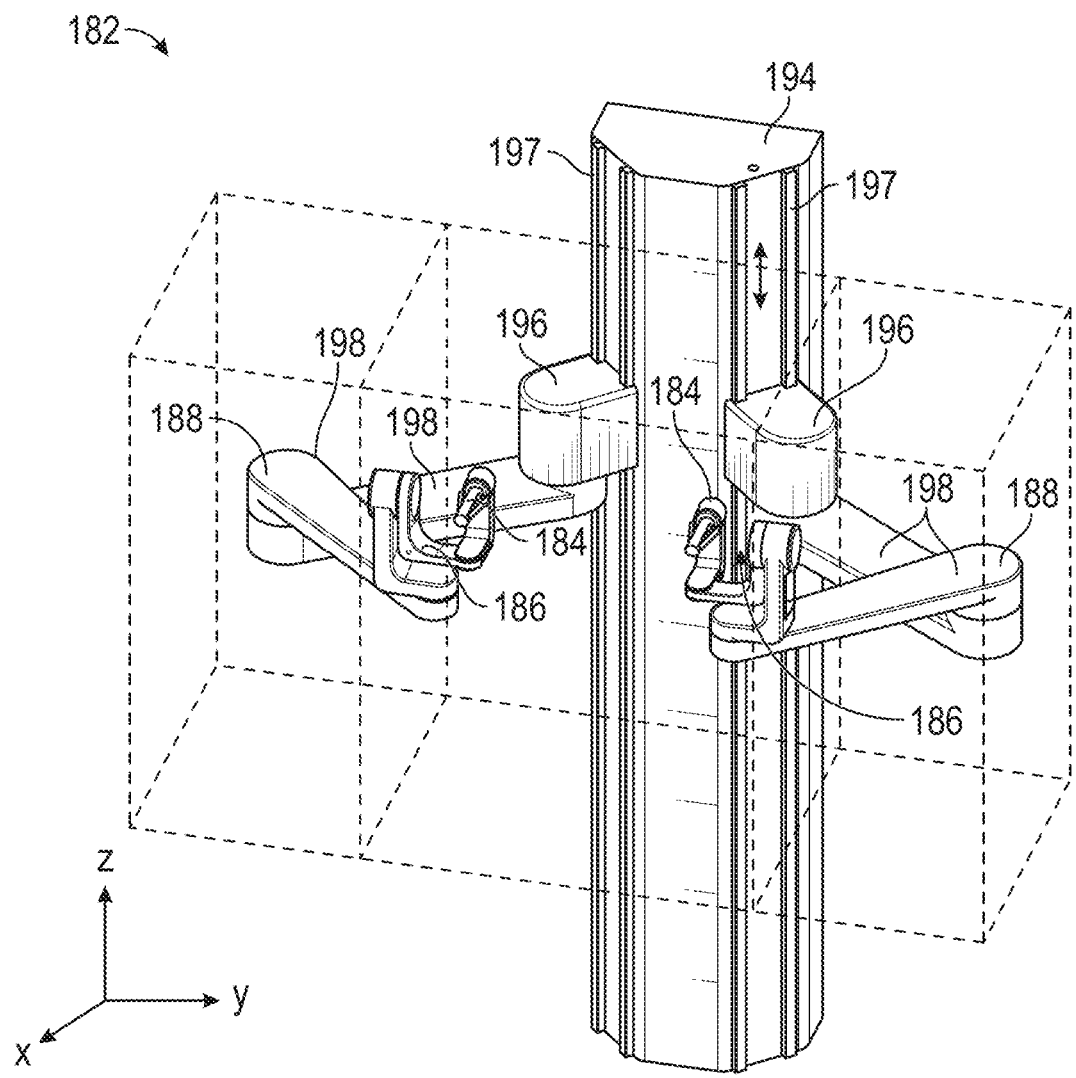
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
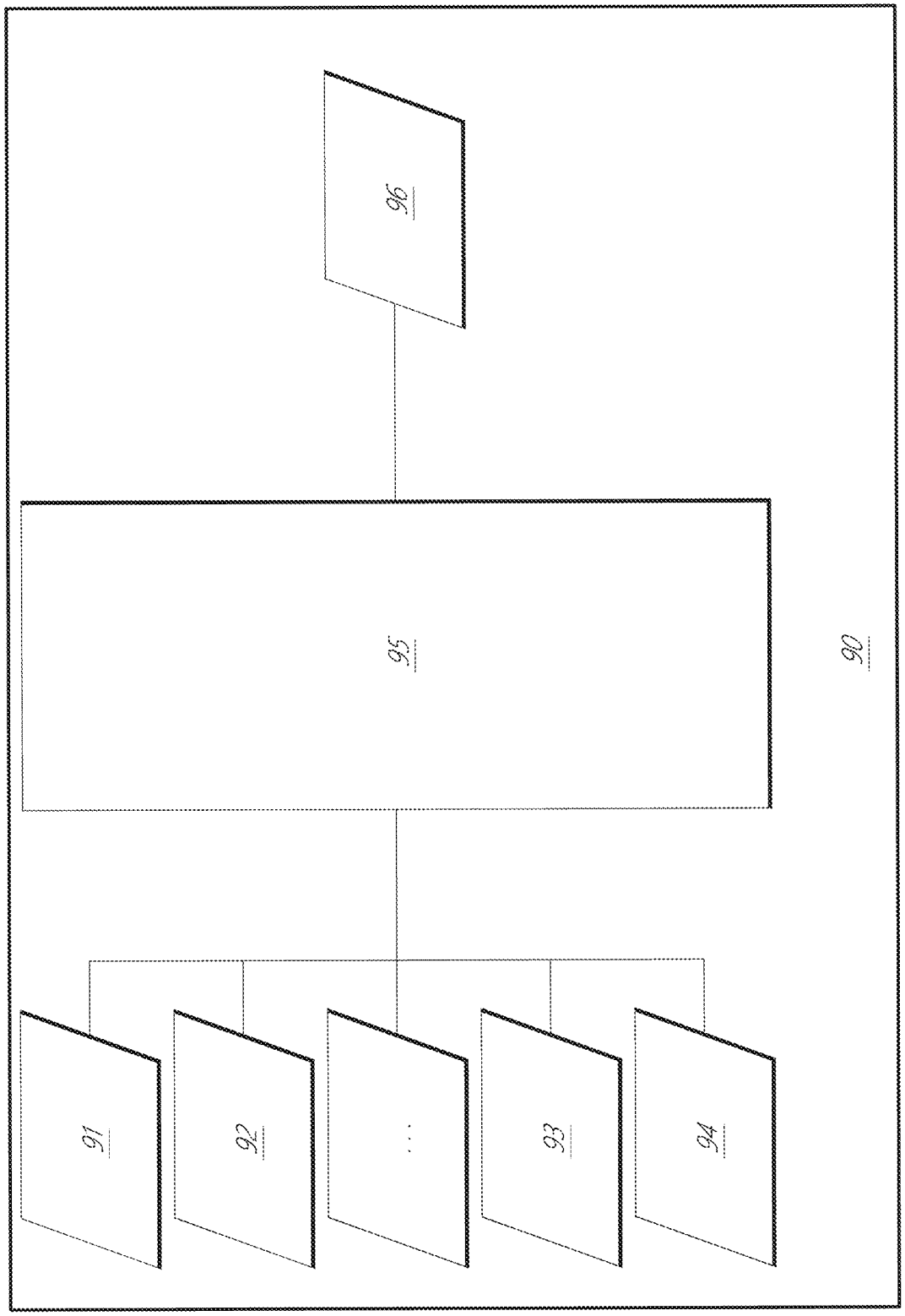
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Manually and Robotically Controllable Medical Instruments

Embodiments of the disclosure relate to devices, systems, and techniques for manually and robotically controllable medical instruments. The manually and robotically controllable medical instruments can be used, in some embodiments, with robotically-enabled medical systems, such as those described above with reference to FIGS. 1-20. As discussed in detail below, the manually and robotically controllable medical instruments can be configured for both manual and robotic control. In this section the term "medical instrument" is intended to refer to a manually and robotically controllable medical instrument unless context indicates otherwise. Such medical instruments can be also considered hybrid medical instruments because they are configured for both manual and robotic control.

In some embodiments, the medical instruments can be configured for endoscopic procedures. For example, the medical instruments can be configured for uroscopy, ureteroscopy, gastroscopy, bronchoscopy, or other endoscopic procedures. In some embodiments, the medical instruments can be configured for laparoscopic procedures or other types of medical procedures (e.g., open procedures).

A. Introduction to Manually and Robotically Controllable Medical Instruments.

In some embodiments, the manually and robotically controllable medical instruments can be operated in a first mode (a manual mode) by a physician or other operator that physically handles and manually manipulates the medical instrument, and can also be operated in a second mode (a robotic mode) by a robotically-enabled medical system. When operated in the manual mode, the physician can manually manipulate one or more manual drive inputs to control the medical instrument. When operated in the robotic mode, the medical instrument can be attached to an instrument drive mechanism that is positioned on the end of a robotic arm or other instrument positioning device. The instrument drive mechanism can include one or more robotic drive outputs that engage one or more robotic drive inputs to robotically control the medical instrument. The physician may use a controller (for example, as shown in FIG. 19) to control the robotically-enabled system.

The medical instruments can include an elongated shaft and an instrument handle (or instrument base). The elongated shaft can be configured for insertion into a patient's anatomy during a medical procedure. In some embodiments, the elongated shaft is inserted into the patient's anatomy through a natural orifice. In some embodiments, the elongated shaft is inserted into the patient's anatomy through an incision or other surgical opening. The elongated shaft can be flexible. The elongated shaft can be articulable and controllable. This can allow an operator, such as a physician, to control the articulation of the elongated shaft so as to navigate and steer the medical instrument through the patient's anatomy. Controlling the articulation of the elongated shaft can include deflecting or bending an articulable portion of the elongated shaft. In some embodiments, the articulable portion can be a distal portion of the elongated shaft.

As described above (for example, with reference to FIGS. 15-18), in some embodiments, the medical instrument can include one or more pull wires extending on or through the elongated shaft. The pull wires can be attached to actuation mechanisms, such as pulleys or pulley assemblies, within the instrument handle. The actuation mechanism can, in turn, be connected to the manual and robotic drive inputs such that actuation of the manual and robotic drive inputs operates the actuation mechanisms to pull on the pull wires to cause articulation of the elongated shaft. In some embodiments, one or more of the manual drive inputs and one or more of the robotic drive inputs are each connected to the same actuation mechanism (e.g., pulley or pulley assembly) within the instrument handle such that both the manual drive input and the robotic drive input can be used to actuate the same actuation mechanism. The manual drive inputs can be separate from the robotic drive inputs. For example, the manual drive inputs can be configured and positioned so as to be hand operable, while the robotic drive inputs can be configured and positioned so as to engage with robotic drive outputs so as to be operable by a robotically-enabled medical system. In some embodiments, the manual drive inputs remain exposed or accessible even when the instrument handle is attached to the instrument drive mechanism.

The medical instruments configured for both robotic and manual control can, in some embodiments, provide one or more advantages. For example, in some embodiments, during a procedure, the medical instruments can first be inserted into the patient manually. That is, a physician may first physically handle and manually insert the medical instrument into the patient using the manual drive inputs to control the articulation of the elongated shaft to guide the medical instrument through the patient's anatomy. A medical instrument that can provide a physician the ability to first perform manual insertion can, in some instances, be quicker and easier than robotic insertion. This can be the case, for example, in certain urological procedures, such as urologic endoscopy, cystoscopy, ureteroscopy, or nephrology, and gastrointestinal endoscopic procedures. After the initial manual insertion, the instrument handle can be attached to the instrument drive mechanism, such as an instrument drive mechanism positioned on the end of a robotic arm or other instrument positioning device or a robotically-enabled medical system. When attached to the robotically-enabled medical system, articulation and control of the elongated shaft of the medical instrument can then be controlled robotically. Robotic control can allow precise and accurate control of the medical instrument at the treatment site. Because certain aspects of medical procedures may be best suited for manual control and other aspects of medical procedures may be best suited for robotic control, the hybrid medical instruments described herein can advantageously be used in either manual or robotic control modes as desired depending on the particular circumstances or stage of the medical procedure. Such medical instruments provide great flexibility to physicians and facilitate performance of the medical procedure.

Additionally, some robotically-enabled medical systems can be limited in absolute insertion depth or stroke. Thus, it may be advantageous to first insert the medical instrument manually such that the finite insertion depth or stroke of the robotic system can be optimally utilized in the area of diagnosis or treatment. The medical instruments described herein can allow the placement of the instrument manually over long distances that would be cumbersome to do robotically. In some embodiments, manual control of the instrument may be used to provide an initial gross positioning for the medical instrument. For example, manual control can be used to position the medical instrument at or near the treatment site within the patient's anatomy, and robotic control of the instrument can be used to provide fine position control during the procedure.

In some embodiments the physician may control the medical instrument manually by operating the manual drive inputs before the medical instrument is attached to the instrument drive mechanism. In some embodiments the physician may control the medical instrument manually by operating the manual drive inputs while the medical instrument is attached to the instrument drive mechanism.

As mentioned above, the medical instruments can include both manual and robotic drive inputs. In some embodiments, one of the manual drive inputs is configured to provide two-way deflection control for the elongated shaft of the medical instrument. Two-way deflection control can allow deflection of the elongated shaft in two directions. In some embodiments, the two directions can be opposite directions, such as up and down or left and right. This can also referred to as two-way deflection control in a single plane, such as an up-down plane or a left-right plane. Directional terms (e.g., up, down, left, right, etc.) in this application are used broadly to indicate different directions relative to the orientation of the medical instrument. Because the medical instrument can be constantly repositioned in a wide variety of orientations, the directional terms should not be interpreted as limiting. For example, the directions referred to as up, down, left, and right can change depending on the orientation of the instrument. The manual drive input configured for two-way deflection control can be, for example, a lever, a slider, a wheel, or other type of manually operable drive input. In some embodiments, manipulating the manual drive input in a first direction causes deflection of the elongated shaft in a first direction (e.g., up) and manipulating the manual drive input in a second direction causes deflection of the elongated shaft in a second direction (e.g., down).

The medical instrument can also include a manual drive input configured to allow roll control for the elongated shaft. This may be referred to as a manual roll input. For example, the medical instrument can include a manual drive input that allows the elongated shaft to be rotated about an axis of the elongated shaft relative to the instrument handle. This manual drive input can be configured to allow reorientation of the elongated shaft radially with respect to the instrument handle. In some embodiments, manual roll control can permit rotation of the elongated shaft of at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, at least 360 degrees, or greater, in both rotational directions. In some embodiments, the manual drive input configured for roll control can be omitted and the physician can physically roll the entire medical instrument (e.g., roll the handle and elongated shaft together) to manually control the roll of the elongated shaft.

Manually controlling the medical instrument using two-way deflection and roll control may be intuitive and familiar to many physicians accustomed to working with medical instruments that are only configured for manual control.

In some embodiments, the medical instrument may include an additional drive input configured to allow an additional two-way deflection control. For example, the first manual drive input can allow two-way deflection control in up and down directions, and the second manual drive input can allow two-way deflection control in left and right directions. This would permit four-way deflection control for the elongated shaft using two manual drive inputs.

In some embodiments, the robotic drive inputs are configured to allow four-way deflection control. In some embodiments four-way deflection control allows articulation of the elongated shaft in four different directions. In some embodiments, the directions can be four orthogonal directions, such as up, down, left, and right. In some embodiments, the robotic drive inputs configured for four-way deflection control can include two robotic drive inputs. The two robotic drive inputs can be configured to engage to with two corresponding robotic drive outputs on the instrument drive mechanism. Each robotic drive input can be rotatable in two opposite directions, for example, clockwise and counterclockwise. Rotation of a first of the two robotic drive inputs in one direction (e.g., the clockwise direction) can allow articulation in one of the four direction (e.g., up). Rotation of the first of the two robotic drive inputs in the opposite direction (e.g., the counterclockwise direction) can allow articulation in another of the four directions (e.g., down). Rotation of a second of the two robotic drive inputs in one direction (e.g., the clockwise direction) can allow articulation in another of the four directions (e.g., right). And rotation of the second of the two robotic drive inputs in the opposite direction (e.g., the counterclockwise direction) can allow articulation in another of the four direction (e.g., left). Thus, four-way deflection control can be achieved using two robotic drive inputs. In some embodiments, the robotic drive inputs are configured to provide other numbers of directional deflection control, such as two-way deflection control, three-way deflection control, etc.

The medical instrument can include an additional robotic drive input configured to provide robotic roll control for the elongated shaft of the medical instrument. For example, the medical instrument can include a robotic drive input configured to engage with a corresponding robotic drive output on the instrument drive mechanism that allows the elongated shaft to be rotated about an axis of the elongated shaft relative to the instrument handle. This robotic drive input can be configured to allow reorientation of the elongated shaft radially with respect to the instrument handle. In some embodiments, rotation of this robotic instrument drive input in a first direction (e.g., clockwise) causes rotation of the elongated shaft in the clockwise direction and rotation of this robotic instrument drive input in a second direction (e.g., counterclockwise) causes rotation of the elongated shaft in the counterclockwise direction. In some embodiments, robotic roll control can permit rotation of the elongated shaft of at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, at least 360 degrees, or greater, in both rotational directions.

In some instances, robotically controlling the medical instrument using four-way deflection control and roll control may be intuitive and familiar to many physicians accustomed to working with robotic instruments that are only configured for robotic control. For example, four way deflection control may be intuitive when operating a controller to control the medical instrument.

As mentioned above, in some embodiments, the medical instruments are configured for manual control that permits manual two-way deflection control and roll control (roll control can be manually achieved either with a manual drive input configured for rolling the elongated shaft relative to the instrument handle or by physically rolling the entire medical instrument) and robotic control that permits robotic four-way deflection control and roll control. Other types of manual and robotic control are also possible. For example, the medical instruments can be configured for manual control that permits manual four-way deflection control and roll control and robotic control that permits robotic four-way deflection control and roll control. As another example, the medical instruments can be configured for manual control that permits manual two-way deflection control and roll control and robotic control that permits robotic two-way deflection control and roll control.

B. Example Embodiments of Manually and Robotically Controllable Medical Instruments.

The above-noted and other features of the manually and robotically controllable medical instruments will now be described with reference to the embodiments illustrated in FIGS. 21A-25. These embodiments are provided by way of example and are intended to be illustrative of the principles of the disclosure without limiting the disclosure. Those of ordinary skill in the art will, upon consideration of this disclosure, appreciate that various modifications of the illustrated embodiments are possible. These modification are intended to be within the scope of this disclosure.

FIGS. 21A-21F illustrate various views of an embodiment of a manually and robotically controllable medical instrument 200. As will be described in greater detail below, the medical instrument 200 is configured for manual two-way deflection control, manual roll control, robotic four-way deflection control, and robotic roll control.

Figure 21A:
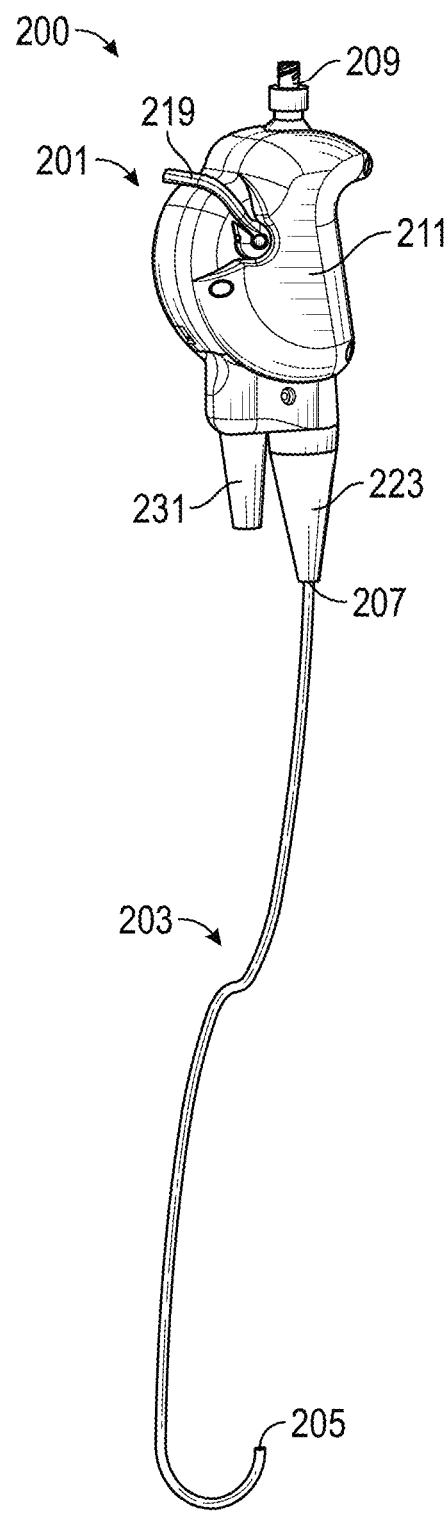
FIGS. 21A-21F illustrate various views of an embodiment of a manually and robotically controllable medical instrument.

FIG. 21A illustrates a perspective view of the medical instrument 200. As illustrated, the medical instrument 200 includes an instrument handle 201 (or instrument base) and an elongated shaft 203. The elongated shaft 203 is configured to be inserted into a patient during a medical procedure. The elongated shaft 203 can be configured to be articulable and controllable, such that the elongated shaft 203 can be navigated and steered through the patient's anatomy. For example, in some embodiments, the elongated shaft 203 comprises a thin, flexible body configured to be inserted into and guided through patient lumens, such as the urethra, ureter, gastrointestinal tract, esophagus, airways of the lungs (etc.). As described above, pull wires can be included in or on the elongated shaft 203 to control articulation of the elongated shaft 203. The elongated shaft 203 can extend between a distal end 205 and a proximal end 207. The distal end 205 can be configured to be inserted into the patient. The proximal end 207 can be attached to the instrument handle 201. The elongated shaft 203 can include a working channel (not illustrated) through which additional instruments or tools can pass for delivery to the distal end 205. The medical instrument 200 can include a working channel entry port 209 configured to allow access to the working channel.

Figure 21C:
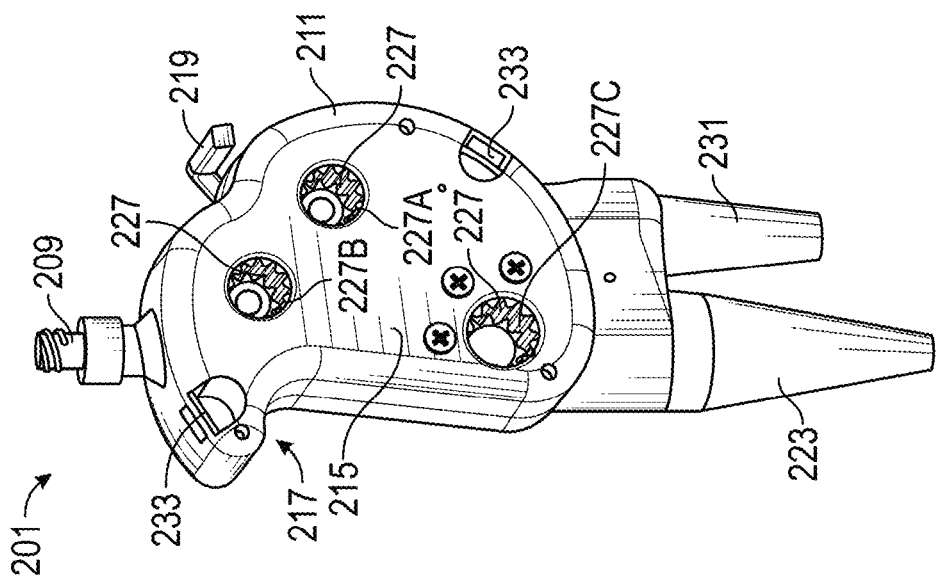
Figure 21B:
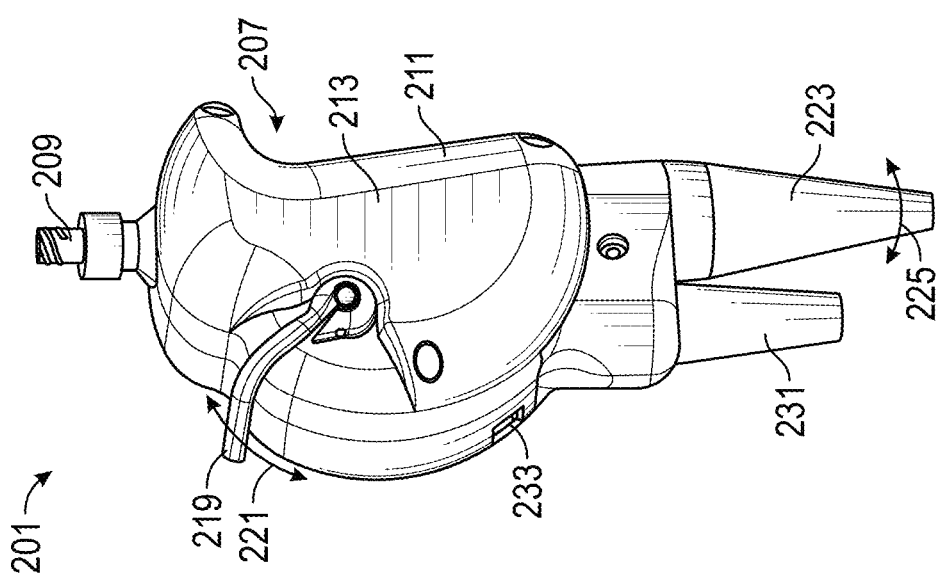

The instrument handle 201 is shown in greater detail in FIGS. 21B and 21C. FIG. 21B illustrates a first side view (e.g., a front view) of the instrument handle 201 and FIG. 21C illustrates a second side view (e.g., a back side view) of the instrument handle 201. The instrument handle 201 is configured to allow both manual control and robotic control of the medical instrument 200. For example, the instrument handle 201 is configured to be physically held and manually manipulated to provide manual control, and to attach to an instrument drive mechanism (see FIGS. 22A-22C described below) to provide robotic control. In some embodiments, a sterile adapter can be positioned between the instrument handle 201 and the instrument drive mechanism to maintain a sterile field during a medical procedure.

Figure 27:
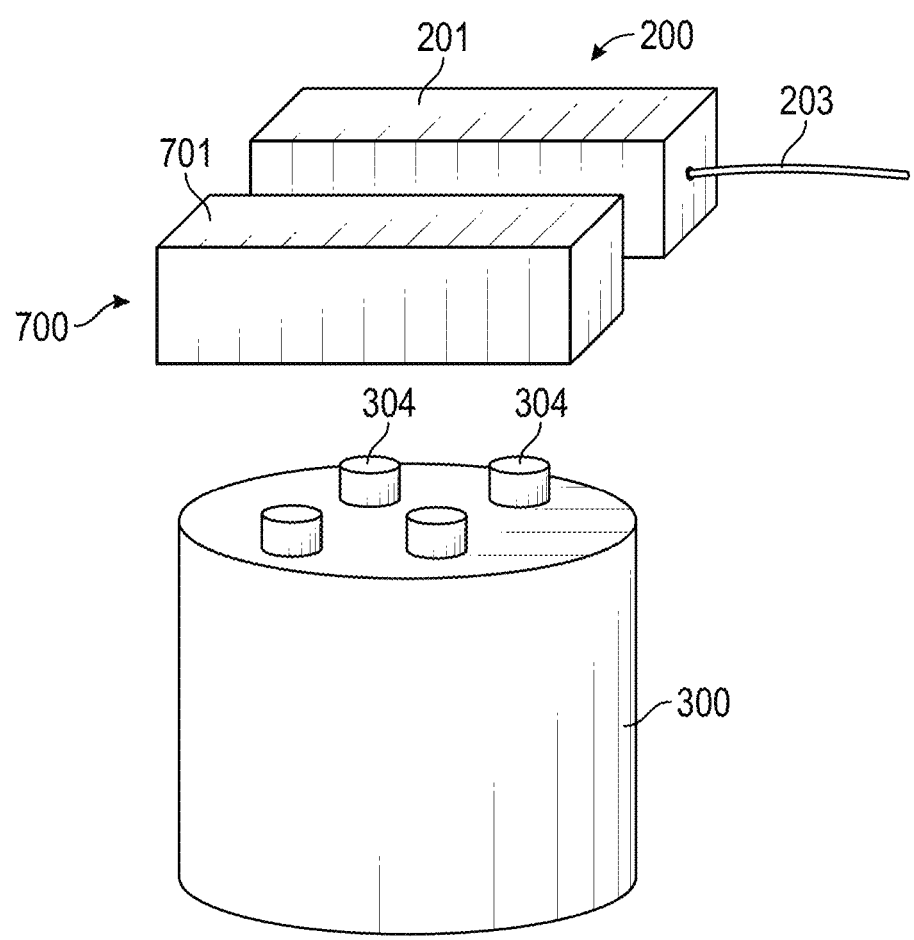
FIG. 27 illustrates a first and a second medical instrument attaching to an instrument drive mechanism.

As illustrated in FIGS. 21A-21C, the instrument handle 201 includes a housing 211. The housing 211 includes a front face 213 (FIG. 21B) and a rear face 215 (FIG. 21C). As illustrated, the housing 211 can also be shaped to include a recessed portion or cutout 217. The cutout 217 can be configured to provide an ergonomic shape for the instrument handle 201. For example, the cutout 217 can allow the instrument handle 201 to be more easily or comfortably held during manual control. Alternatively or additionally, the cutout 217 can provide (or not block) access to one or more unused robotic drive outputs on the instrument drive mechanism as will be described below with reference to FIGS. 22A-22C. As shown in FIG. 27, this can allow more than one medical instrument (e.g., two medical instruments) to be connected to a single instrument drive mechanism, such that the instrument drive mechanism can be used to drive more than one medical instrument. The robotic drive outputs that remain exposed due to the cutout 217 can then be used to control additional instruments or tools during a procedure.

FIGS. 21A-21C illustrate that the instrument handle 201 can include a manual drive input 219. In the illustrated embodiment, the manual drive input 219 is configured as a lever, although other mechanical structures such as sliders or wheels are possible. As will be described in greater detail below, the manual drive input 219 is configured to provide manual two-way deflection control for the medical instrument 200. In the illustrated embodiment, the manual drive input 219 is configured to be manipulated or rotated back and forth in the directions illustrated by the arrows 221 (FIG. 21B). Moving the manual drive input 219 in a first direction can cause articulation of the elongated shaft 203 in a first articulation direction, and moving the manual drive input 219 in a second direction (opposite the first direction) can cause articulation of the elongated shaft 203 in a second articulation direction. The first and second articulation directions can be substantially opposite (e.g., up and down), although this need not be the case in all embodiments.

In the illustrated embodiment, the instrument handle 201 also includes a manual roll input 223. As shown in FIG. 21A, the distal end 207 of the elongated shaft 203 can be attached to the manual roll input 223. In some embodiments, the elongated shaft 203 extends through the manual roll input 223 and into the housing 211. The manual roll input 223 is configured to allow the elongated shaft 203 to rotate relative to the instrument handle 201. As illustrated, the manual roll input 223 can be a twister or rotatable handle or grip that can rotate relative to the housing 211. For example, the manual roll input 223 can rotate in the directions illustrated by the arrows 225. In some embodiments, the manual roll input 223 rotates in both the clockwise and counterclockwise directions. The elongated shaft 203 can be rotationally fixed relative to the manual roll input 223 such that rotation of the manual roll input 223 causes rotation of the elongated shaft 203. Rotation of the elongated shaft 203 can be in the same direction and equal to corresponding motion of the manual roll input 223, although this need not be the case in all embodiments.

With reference to FIG. 21C, which shows a rear view of the instrument handle 201, the medical instrument 200 includes a plurality of robotic drive inputs 227. In the illustrated embodiment, the medical instrument 200 includes three robotic drive inputs 227, although other numbers of robotic drive inputs 227 can be used in other embodiments. The robotic drive inputs 227 are configured to engage corresponding robotic drive outputs on an instrument drive mechanism when the instrument handle 201 is attached to the instrument drive mechanism. Example robotic drive outputs and instrument drive mechanisms are shown in FIGS. 15-17 (described above) and FIGS. 22A and 22B (described below). The robotic drive outputs of the instrument drive mechanism engage and transfer torque to or rotate the robotic drive inputs 227. In some embodiments, each of the robotic drive inputs 227 are rotatable in both the clockwise and counterclockwise directions. In the illustrated embodiment, the robotic drive inputs 227 are configured as grooved or keyed recesses and are configured to engage robotic drive outputs that are configured as protruding splines. The robotic drive outputs can be driven by motors to rotate in clockwise and counterclockwise directions. When the robotic drive outputs are engaged with the robotic drive inputs 227, the robotic drive inputs transfer rotational motion to the robotic drive inputs 227. In some embodiments, the robotic drive outputs drive the robotic drive inputs 227. In some embodiments, this arrangement can be reversed or other types and configurations of robotic drive inputs and outputs can be used.

As mentioned above, the illustrated embodiment of the medical instrument 200 is configured for robotic four-way deflection control and robotic roll control. In this embodiment, two of the robotic drive inputs 227 are configured for deflection control, and the other of the robotic drive inputs 227 is configured for roll control. Each of the two of the robotic drive inputs 227 configured for deflection control can permit two-way deflection control so that, together, four-way deflection control can be achieved.

In the illustrated embodiment, a first robotic drive input 227a and a second robotic drive input 227b are each configured to provide two-way deflection control, such that the medical instrument 200 is capable of four-way deflection control. For example, rotation of the first robotic drive input 227a in a first rotational direction (e.g., clockwise) can provide articulation of the elongated shaft 203 in a first articulation direction, and rotation of the robotic drive input 227a in a second rotational direction (e.g., counterclockwise) can provide articulation of the elongated shaft 203 in a second articulation direction. In some embodiments, the first and second articulation directions can be substantially opposite (e.g., up and down), although this need not be the case in all embodiments. Rotation of the second robotic drive input 227b in a first rotational direction (e.g., clockwise) can provide articulation of the elongated shaft 203 in a third articulation direction, and rotation of the robotic drive input 227b in a second rotational direction (e.g., counterclockwise) can provide articulation of the elongated shaft 203 in a fourth articulation direction. In some embodiments, the third and fourth articulation directions can be substantially opposite (e.g., left and right), although this need not be the case in all embodiments. Further, in some embodiments, the first, second, third, and fourth articulations can be substantially orthogonal directions.

As will be described in more detail below, in some embodiments, actuation of the first robotic drive input 227a is configured to cause the same articulation of the elongated shaft 203 as actuation of the manual drive input. For example, both the first robotic drive input 227a and the manual drive input 219 can be configured to cause articulation of the elongated shaft 203 in up and down direction. This can be because, as will be described with reference to FIGS. 21D-21F, both the first robotic drive input 227a and the manual drive input 219 can be connected to the same articulation mechanism (e.g., the first pulley assembly 229) within the housing 211 of the instrument handle 201. In some embodiments, the two-way deflection control provided by the manual drive input 219 is the same as the two-way deflection control provided by the first robotic drive input 227a.

As shown in FIGS. 21A-21C, the instrument handle 201 of the medical instrument 200 can also include a connector 231 for providing electrical and/or visual connections to the medical instrument 200. In the illustrated embodiment, connector 231 is illustrated as a strain relief for an umbilical cable that leads to a connector at a tower. FIG. 21C shows that the rear face 215 may include one or more latching mechanisms 233 for orienting and securing the instrument handle 201 to the instrument drive mechanism.

Figure 21D:
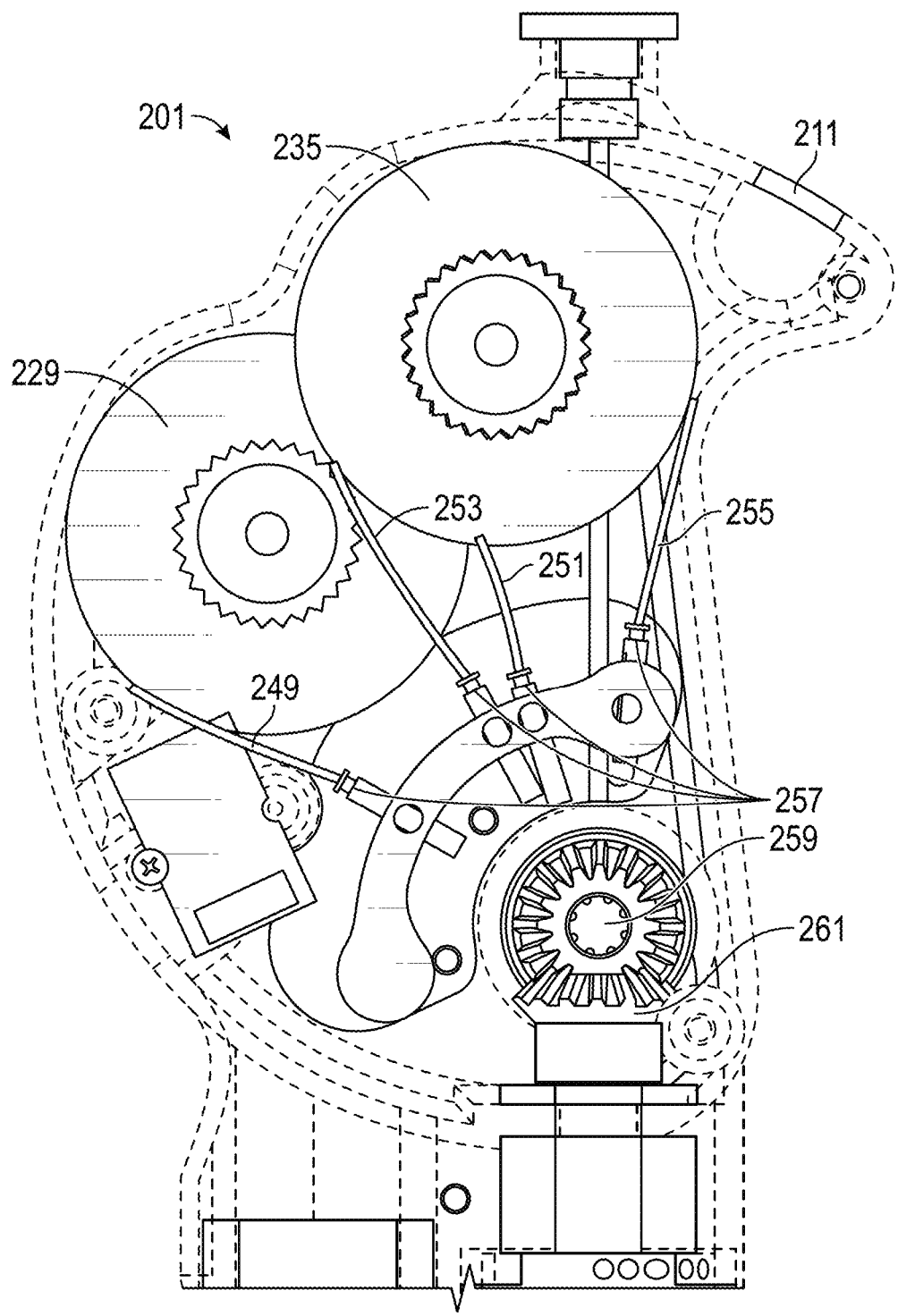
Figure 21E:
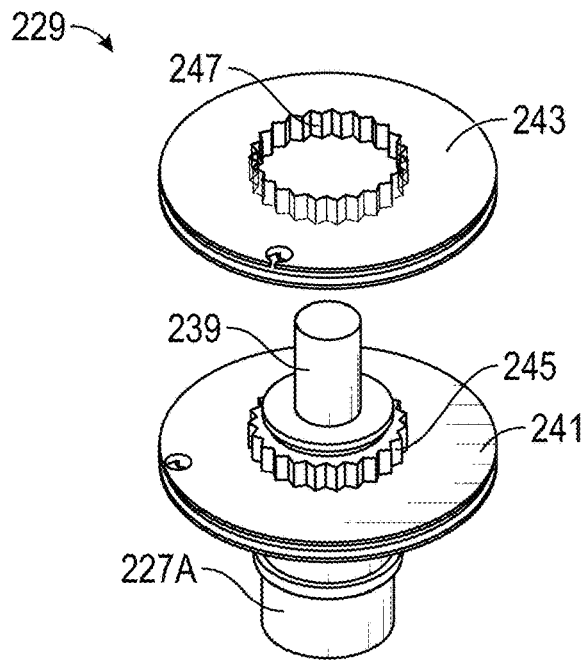
Figure 21F:
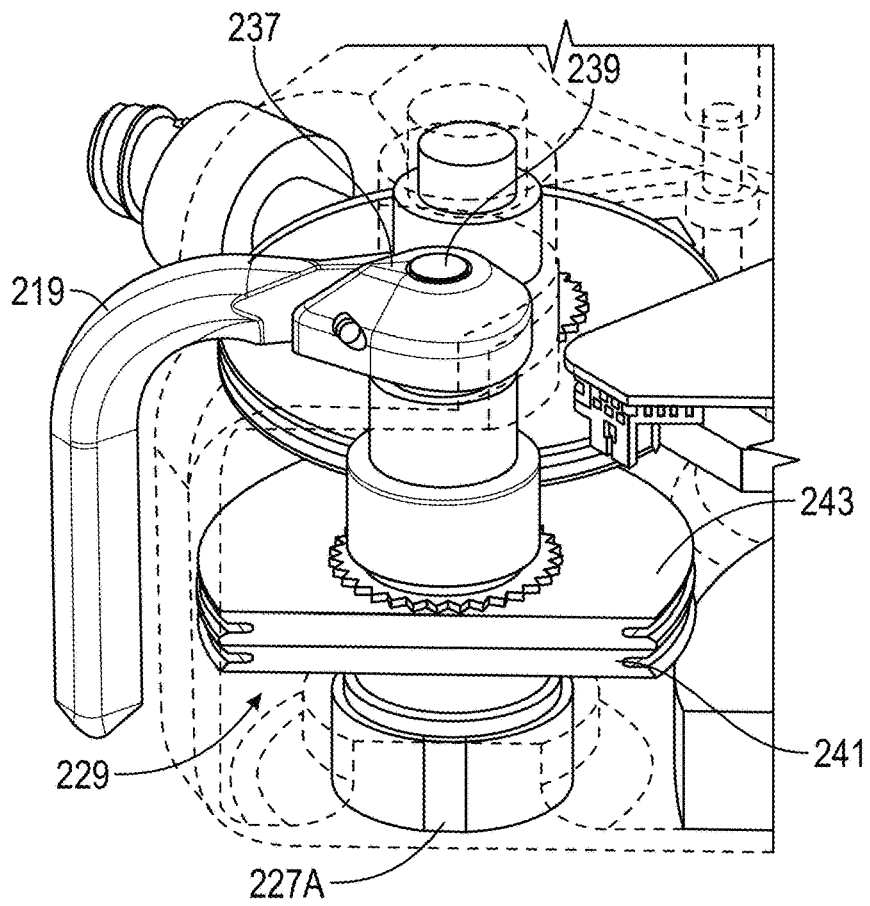

FIGS. 21D-21F illustrate some of the internal components of the instrument handle 201. FIG. 21D illustrates a first side view of the instrument handle 201 with the housing 211 shown as transparent so as to view the internal components. As shown, two pulley assemblies, first pulley assembly 229 and second pulley assembly 235, are positioned within the housing 211. In this embodiment, each of the first pulley assembly 229 and the second pulley assembly 235, is associated with two of four articulation directions of the elongated shaft. In some embodiments, each plane of articulation (e.g., up-down or left-right) can be linked to one pulley assembly. For example, up and down articulation of the elongated shaft 203 can be associated with the first pulley assembly 229 and left and right articulation of the elongated shaft 203 can be associated with the second pulley assembly 235.

In the illustrated embodiment, the first pulley assembly 229 is rotationally coupled to the first robotic drive input 227a and the second pulley assembly 235 is rotationally coupled to the second robotic drive input 227b. Rotation of the first robotic drive input 227a can thus cause corresponding rotation of the first pulley assembly 229, and rotation of the second robotic drive input 227b can cause corresponding rotation of the second pulley assembly 229. As noted above, rotation of the first pulley assembly 229 can cause articulation of the elongated shaft 203 in the up and down directions, and rotation of the second pulley assembly 235 can cause articulation of the elongated shaft 203 in the left and right directions. Thus, for some embodiments, robotic four-way deflection control can be achieved with the first and second robotic drive inputs 227a. 227b and the first and second pulley assemblies 229, 235. Alternatively, four separate pulleys could be used with four corresponding robotic drive inputs.

As shown in FIG. 21F, the manual deflection input 219 can also be rotationally coupled to the first pulley assembly 229 such that the manual deflection input 219 can be used to rotate the first pulley assembly 229. As noted above, rotation of the first pulley assembly 229 can cause articulation of the elongated shaft 203 in the up and down directions. Thus, in the illustrated embodiment, both the manual drive input 219 and the first robotic drive input 227a are each rotationally coupled to the first pulley assembly 229, such that both can cause articulation of the elongated shaft 203 in, for example, the up and down directions. In the illustrated embodiment, the manual drive input 219 is configured as a lever that is rigidly attached to the first pulley assembly 229. For example, as shown in FIG. 21F, an end 237 of the manual drive input 219 is attached to a shaft 239 of the first pulley assembly 229. Thus, any motion of the manual drive input 219 can be directly transferred to the first pulley assembly 229. Accordingly, the medical instrument 200 is configured for manual two-way deflection control (with the manual drive input 219) and four-way deflection control (with the first and second robotic drive inputs 227a, 227b).

In the illustrated embodiment, the second pulley assembly 235 is only articulable with the second robotic drive input 227b. In some embodiments, a second manual drive input (not illustrated) can be rotationally coupled to the second pulley assembly 235 to further allow manual control of the elongated shaft in, for example, the left and right directions.

An example first pulley assembly 229 is illustrated with an exploded view in FIG. 21E. In some embodiments, the second pulley assembly 235 may be similar. As illustrated, the first pulley assembly 229 includes a first pulley 241 and a second pulley 243. The first pulley 241 can be fixedly attached or otherwise mounted on a shaft 239 of the first pulley assembly 229 such that the first pulley 241 and the shaft 239 rotate together. The second pulley 243 can be configured to be removably attachable to the shaft 239. When attached, the second pulley 243 and the shaft 239 (as well as the first pulley 241) can all rotate together. In the illustrated embodiment, the shaft 239 includes a keyed portion 245 configured to engage with a keyed portion 247 on the second pulley 243. The keyed portion 245 is configured to engage the keyed portion 247 to rotationally couple the second pulley 243 to the shaft 239. In some embodiments, the keyed portion 245 is configured to engage the keyed portion 247 in a plurality of different rotational positions, such the rotational position of the second pulley 243 and be adjusted and set relative to the rotational position of the first pulley 241. In some embodiments, the keyed engagement allows rotational adjustment of the second pulley 243 relative to the first pulley in rotational increments of 5, 10, 15, 20, 25, 30, 35, 40, 45 degrees, for example.

As illustrated in FIG. 21E, one end of the shaft 239 can be connected to the first robotic drive input 227a. Thus, rotation of the first robotic drive input 227a can be configured to cause rotation of the first pulley assembly 229, including rotation of both the first pulley 241 and the second pulley 243. As illustrated in FIG. 21F, the opposite end of the shaft 239 can also be connected to the manual drive input 219. Thus, rotation of the manual drive input 219 can also be configured to cause rotation of the first pulley assembly 229, including rotation of both the first pulley 241 and the second pulley 243.

As mentioned above, the medical instrument 200 may include pull wires for articulating the elongated shaft 203. In some embodiments, one pull wire can be associated with each direction of articulation of the elongated shaft 203. In some embodiments, the medical instrument 200 includes four pull wires, such that four-way deflection control is possible. In such cases, for example, a first pull wire can be associated with deflection in an up direction, a second pull wire can be associated with deflection in a down direction, a third pull wire can be associated with deflection in a right direction, and a fourth pull wire can be associated with deflection in a left direction. The pull wires can extend between the first and second pulley assemblies 229, 235 and the distal end 205 of the elongated shaft 203. At the distal end 205, the pull wires can be connected to the distal end 205 of the elongated shaft 203.

At the first and second pulley assemblies 229, 235 each of the pull wires can be wound, wrapped, or otherwise mounted on or connected to the one of the pulleys of the two pulley assemblies. For example, considering the first pulley assembly 229 as shown in FIG. 21E, the first pull wire (e.g., associated with upward deflection) can be wound on the first pulley 241 and the second pull wire (e.g., associated with downward deflection) can be wound on the second pulley 243. The first pull wire can be wound on the first pulley 241 in a first direction (e.g., clockwise) and the second pull wire can be wound on the second pulley 243 in a second, opposite direction (e.g., counter clockwise). This allows rotation of the first pulley assembly 229 to pull on either the first pull wire (e.g., to cause upward deflection) or the second pull wire (e.g., to cause downward deflection) depending on the direction that the first pulley assembly 229 is rotated. The third and fourth pull wires can similarly be wound on the pulleys of the second pulley assembly 235 for, for example, left and right deflection control. An example, of this arrangement of pull wires is shown in FIG. 21D, which shows, a first pull wire 249 and a second pull wire 251 wound on the first pulley assembly 229 in opposite directions and a third pull wire 253 and a second pull wire 255 wound on the second pulley assembly 235 in opposite directions.

In some embodiments, the pull wires are routed to adjustable stoppers 257 that allow for fine adjustment of pull wire tension. Gross adjustment of pull wire tension is possible by selectively rotationally positioning the second pulley 243 relative to the first pulley 241 using the keyed engagement features of keyed portions 245, 247. In some embodiments, a spring can additionally or alternatively be used to apply tension to each pull wire. In some embodiments, coil pipes, not shown, extend from the adjustable stoppers 257, down through the elongated shaft 203, and to the distal end 205. The pull wires and coil pipes can include service loops (e.g., extra length) to allow for roll of the elongated shaft 203. In some embodiments, the service loops permit roll of the elongated shaft in both rotational directions of at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, or at least 360 degrees. In some embodiments, the pull wires can extend through lumens braided into or otherwise formed into the elongated shaft 203.

As best seen in FIG. 21D, in the illustrated embodiment, robotic shaft roll can be achieved by first bevel gear 259 and a second bevel gear 261. The first bevel gear 259 can be attached to the third robotic drive input 227c (FIG. 21C), such that rotation of the third robotic drive input 227 can cause rotation of the first bevel gear 259. The second bevel gear 261 can be attached to the proximal end 207 of the elongated shaft 203 such that rotation of the second bevel gear 261 can cause rotation of the elongated shaft 203 relative to the instrument handle 201. The first and second bevel gears 259, 261 can be engaged to transfer rotational movement of the third robotic drive input 227c to the elongated shaft 203. Other methods and mechanisms for transferring rotational motion of the third robotic drive input 227c to the elongated shaft 203 are also possible. In some embodiments, as the elongated shaft 203 is rolled, the internal components (such as the coil pipes, pull wires, electrical wires, and fiber optics) are allowed to twist as they are fixed on both proximal end 207 and distal end 205. Twisting of the internal components can be achieved throughout much of the length of the elongated shaft 203, minimizing the resultant force/torque applied to the proximal and distal terminations.

Thus, the medical instrument 200 illustrated in FIGS. 21A-21F can be configured for manual two-way deflection control, manual roll control, robotic four-way deflection control, and robotic roll control.

Figure 22A:
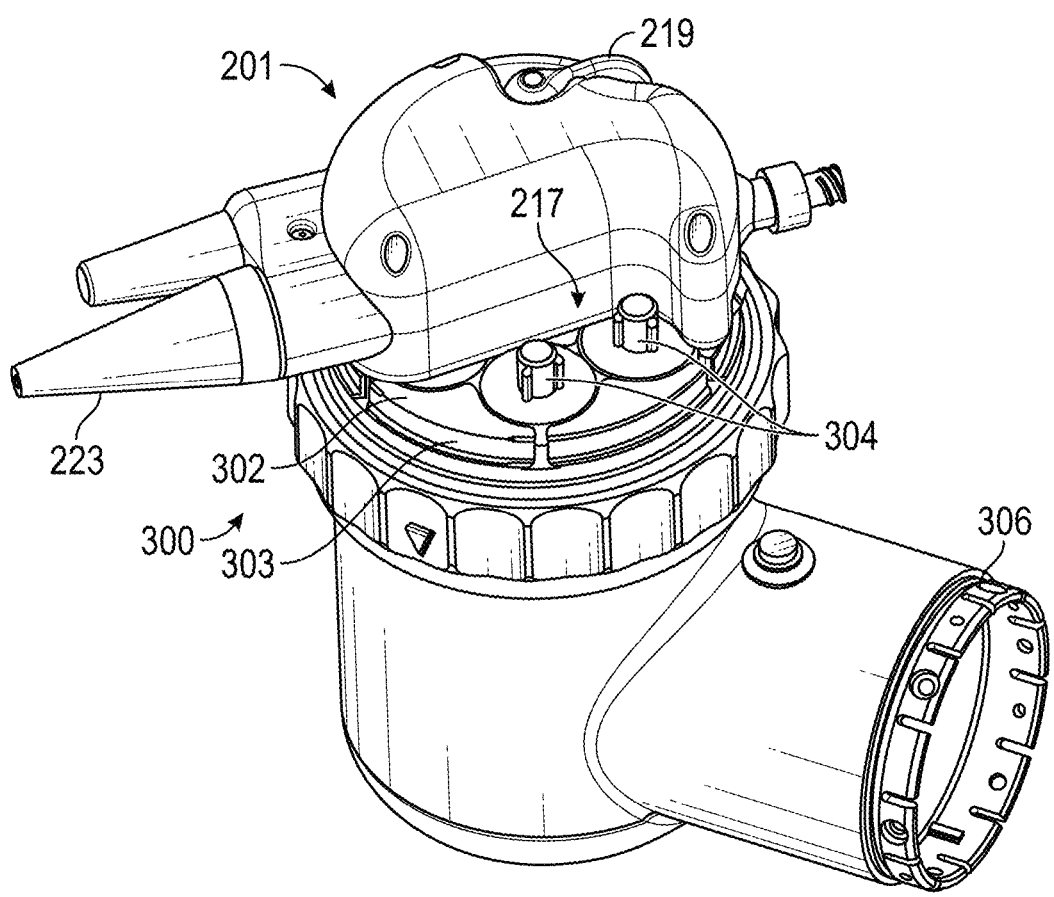
FIGS. 22A-22C illustrate views of the instrument handle of the medical instrument of FIG. 21A attached to an embodiment of an instrument drive mechanism.
Figure 22B:
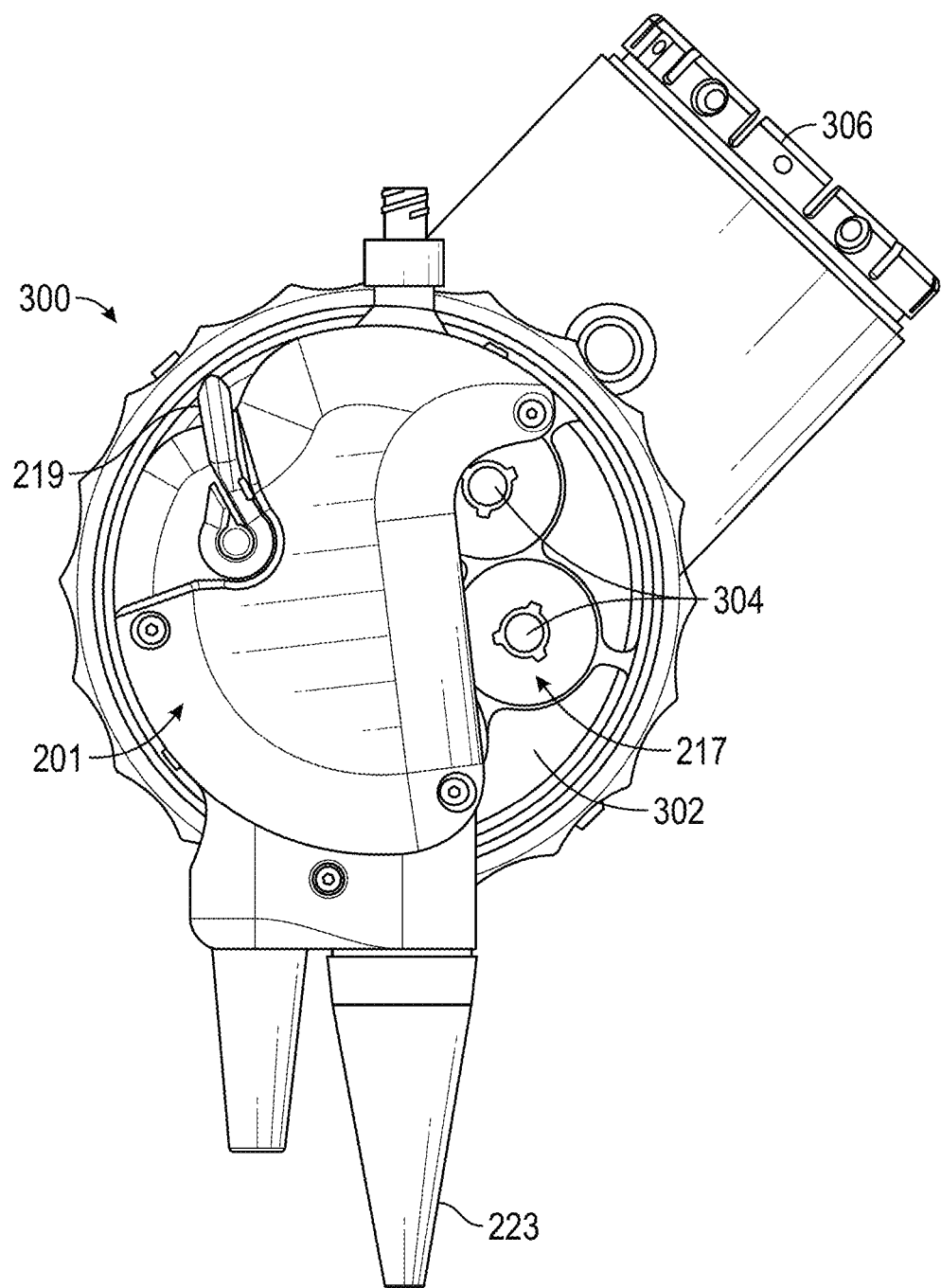
Figure 22C:
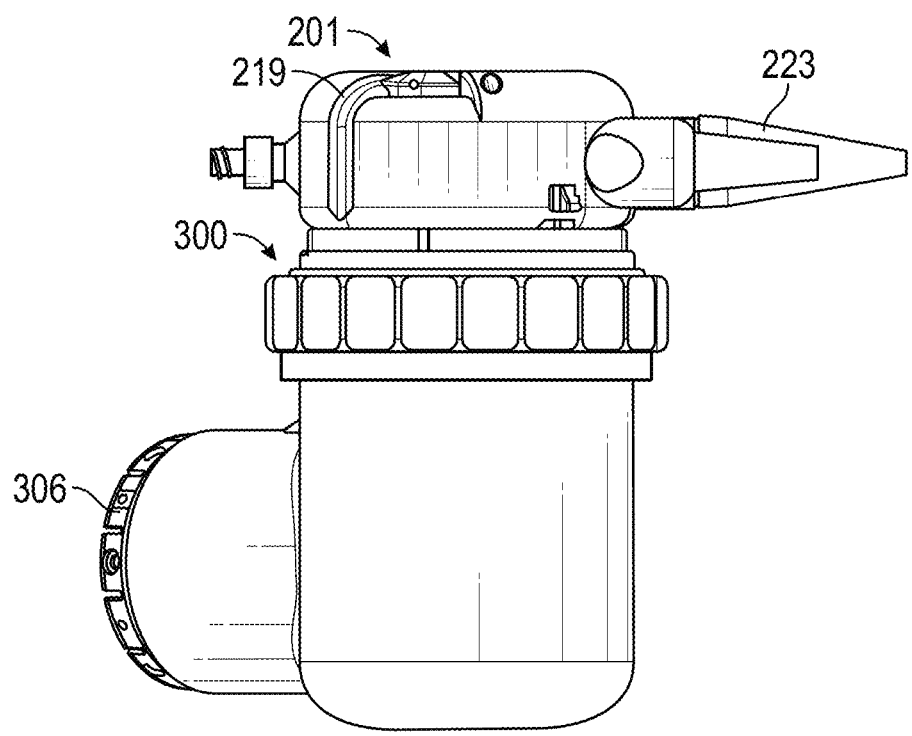

FIGS. 22A-22C illustrate views of the instrument handle 201 of the medical instrument 200 attached to an embodiment of an instrument drive mechanism 300. FIG. 22A is a perspective view, FIG. 22B is a top view, and FIG. 22C is a side view. The elongated shaft 203 of the medical instrument 200 is not illustrated in these figures. The instrument drive mechanism 300 can include a distal face 302 to which the instrument handle 201 can be attached. In some embodiments, a separate adapter (such as sterile adapter 303) can be positioned between the instrument handle 201 and the instrument drive mechanism 300. The sterile adapter can provide a sterile boundary between the instrument handle 201 and the instrument drive mechanism 300. The distal face 302 can include robotic drive outputs 304 positioned thereon. One or more of the robotic drive outputs 304 can engage the robotic drive inputs 227 (FIG. 21C) of the instrument handle 201. As illustrated in FIGS. 22A-22C, the cutout 217 of the instrument handle 201 can leave one or more of the robotic drive outputs 304 exposed. The exposed robotic drive outputs 304 can thus remain accessible to be connected to other medical instruments or tools. The instrument drive mechanism 300 can include one or more motors for driving the robotic drive outputs 304 as shown, for example, in FIG. 15. In the illustrated embodiment, the robotic drive outputs 304 are configured as protruding splines. A proximal end 306 of the instrument drive mechanism 300 can be configured to attach to a robotic arm or other instrument positioning device as shown, for example, in FIGS. 16 and 17.

FIG. 27 illustrates that two medical instruments (e.g., medical instrument 200 and another tool or medical instrument 700) can be configured to engage with and be driven by a single instrument drive mechanism 300. In the illustrated embodiment, the instrument drive mechanism 300 includes four robotic drive outputs 304, although other numbers of drive outputs are possible. The robotic drive outputs 304 can be configured to engage corresponding robotic drive inputs on the two medical instruments 200, 700. For example, some of the drive outputs 304 can engage drive inputs on the medical instrument 200 and some of the drive outputs 304 can engage drive inputs on the medical instrument 700. This can allow the instrument drive mechanism 300 to drive both medical instruments 200, 700. As illustrated, the medical instruments 200, 700 can be positioned side by side on the instrument drive mechanism 300 or the second medical instrument 700 can be positioned within the cutout 217 of the first medical instrument 200 as mentioned above. The medical instruments 200, 700 can be any of the medical instruments or tools described herein.

As illustrated in FIG. 27, a robotic medical system can include the first medical instrument 200, the second medical instrument 700, and the instrument drive mechanism 300. The first medical instrument 200 can include a first instrument handle or base 201 and an elongated shaft 203 extending from the instrument base 201. The instrument base 201 can include at least one first robotic drive input (for example, one, two, three, four, or more robotic drive inputs). The second medical instrument 700 (or other tool) can also include a second instrument base 701 and at least one second robotic drive input (for example, one, two, three, four, or more robotic drive inputs), the instrument drive mechanism 300 can be engaged with first instrument base 201 of the first medical instrument 200 and the second instrument base 701 of the second medical instrument 700. The at least one first robotic drive output 304 can be engaged with and configured to drive the at least one first robotic drive input of the first medical instrument 200, and the at least one second robotic drive output 304 can be engaged with and configured to drive the at least one second robotic drive input of the second medical instrument 700. In this manner, the instrument drive mechanism 300 can drive both medical instruments 300. For example, the instrument drive mechanism 300 can, for example, cause articulation of the medical instruments 200, 700 (if the instruments are articulable) or execute or actuate any other robotically controllable feature or function of the medical instruments.

The instrument drive mechanism 300 can be positioned on a robotic arm. The robotic arm can be configured to move the instrument drive mechanism 300 to reposition the first medical instrument 200 and the second medical 300 instrument simultaneously.

During use of the system shown in FIG. 27, the first instrument base 201 of the first medical instrument 200 can be attached to the instrument drive mechanism 300 such that the robotic drive output(s) 304 of the instrument drive mechanism 300 engage the first robotic drive input(s) of the first instrument base 201. The first instrument base 201 can be configured such that one or more of the robotic drive outputs 304 remains exposed. The second instrument base 701 of the second medical instrument 700 can be attached to the instrument drive mechanism 300 such that the exposed robotic drive output(s) 304 of the instrument drive mechanism 300 engage the robotic drive input(s) of the second instrument base 701. The system (or an operator of the system) can then actuate the first medical instrument 200 and/or the second medical instrument 700 with the instrument drive mechanism 300.

In some embodiments, as illustrated in FIGS. 22A-22C, when the instrument handle 201 is attached to the instrument drive mechanism 300, the manual drive input 219 and the manual roll input 223 remain exposed and accessible.

In some embodiments, the instrument 200 can be configured such that connection of the instrument handle 201 to the instrument drive mechanism 300 causes disengagement of the manual drive input 219. For example, in some embodiments, prior to connecting the instrument handle 201 to the instrument drive mechanism 300, the manual drive input 219 is operably connected to the pulley assembly 229 such that the manual drive input 219 can be actuated to cause articulation of the instrument 200 as described above. In some embodiments, after the instrument handle 201 is connected to the instrument drive mechanism 300, the manual drive input 219 is disengaged from the pulley assembly 229 such that the manual drive input 219 is not useable to articulate the instrument 200 while the instrument handle 201 is connected to the instrument drive mechanism 300.

In some embodiments, connection of the instrument handle 201 to the instrument drive mechanism 300 causes disengagement of the manual drive mechanism. Disengagement may be automatic. For example, inserting a robotic output 304 of the instrument drive mechanism 300 into a robotic input 227 of the instrument handle 201 can cause disengagement by, for example, disengaging the end 237 of the manual drive input 219 from the shaft 239 of the pulley assembly 229 (see FIG. 21F). In another embodiment, a clutch mechanism can be positioned between the manual drive input 219 and the pulley assembly 229 and/or robotic drive input 227. Connecting the instrument handle 201 to the instrument drive mechanism 300 can disengage the clutch mechanism. In some embodiments, a user input can be included that is user-actuable to disengage the manual drive input 219. In some embodiments, the manual drive input 219 can be reengaged when the instrument 200 is removed from the instrument drive mechanism 300.

FIGS. 23A-23H illustrate various views of another embodiment of a manually and robotically controllable medical instrument 400. As will be described in greater detail below, the medical instrument 400 is configured for manual two-way deflection control, manual roll control, robotic four-way deflection control, and robotic roll control.

Figure 23A:
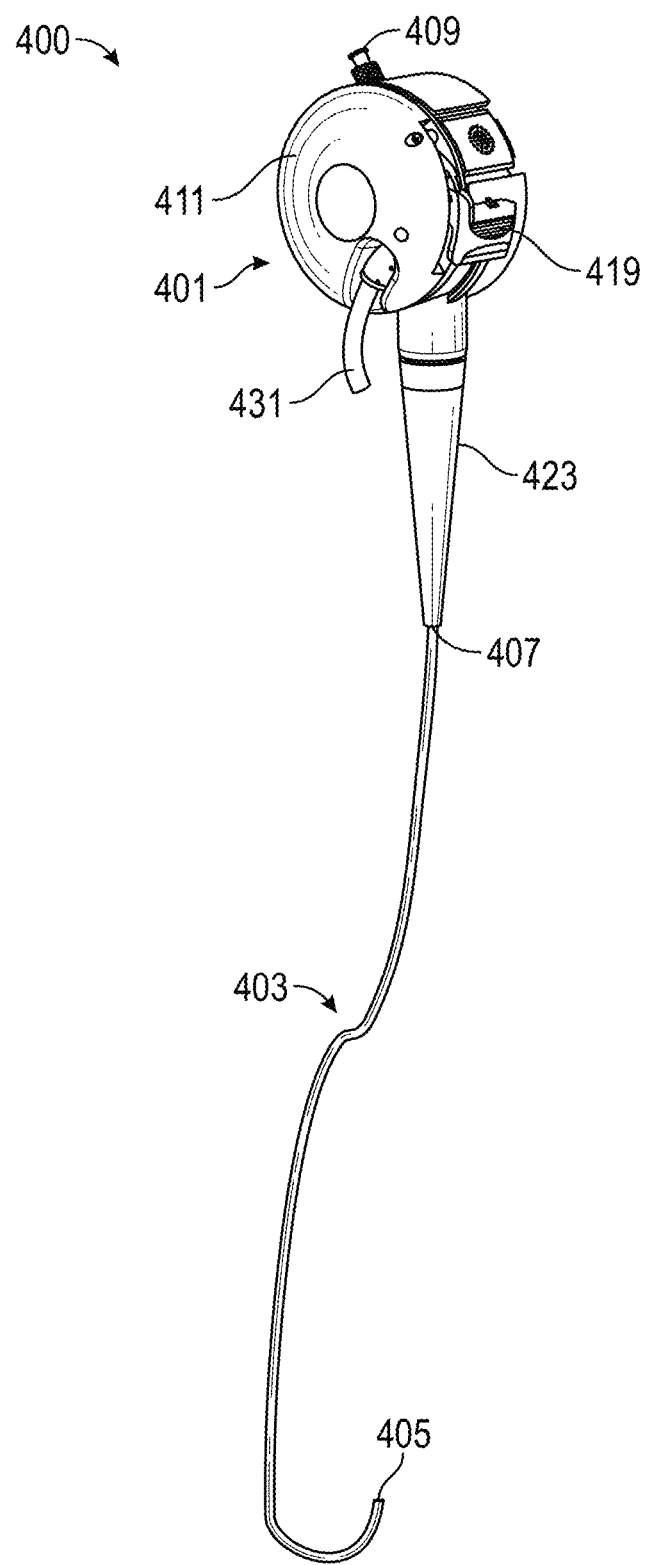
FIGS. 23A-23H illustrate various views of another embodiment of a manually and robotically controllable medical instrument.

FIG. 23A illustrates a perspective view of the medical instrument 400. In some respects similar to the medical instrument 200, the medical instrument 400 includes an instrument handle 401 and an elongated shaft 403. The elongated shaft 403 can extend between a distal end 405 and a proximal end 407. The distal end 405 can be configured to be inserted into the patient. The proximal end 407 can be attached to the instrument handle 401. The elongated shaft 403 can include a working channel (e.g., through the second bevel gear 461, see FIG. 23D) and an entry port 409 configured to allow access to the working channel.

Figure 23B:
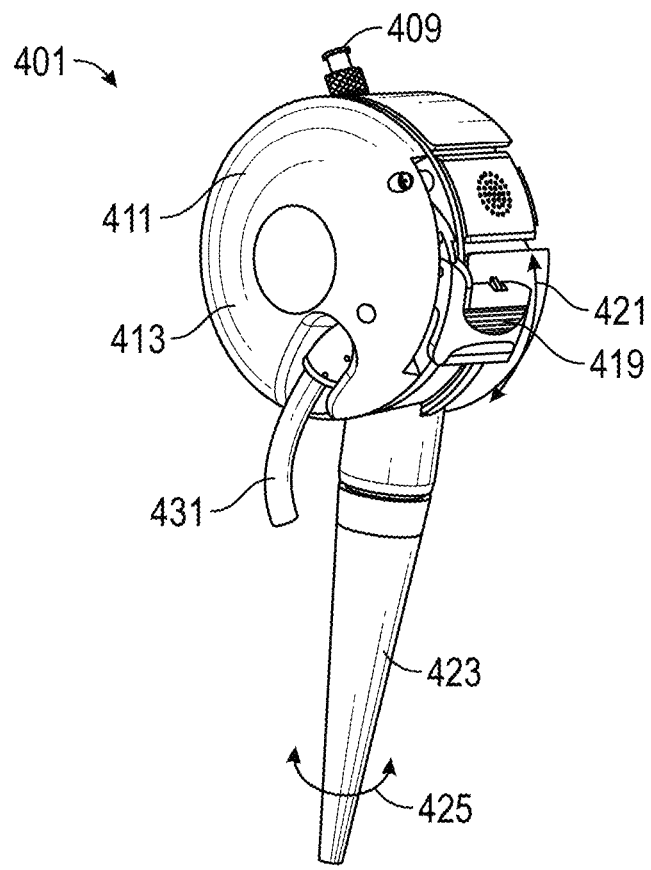
Figure 23C:
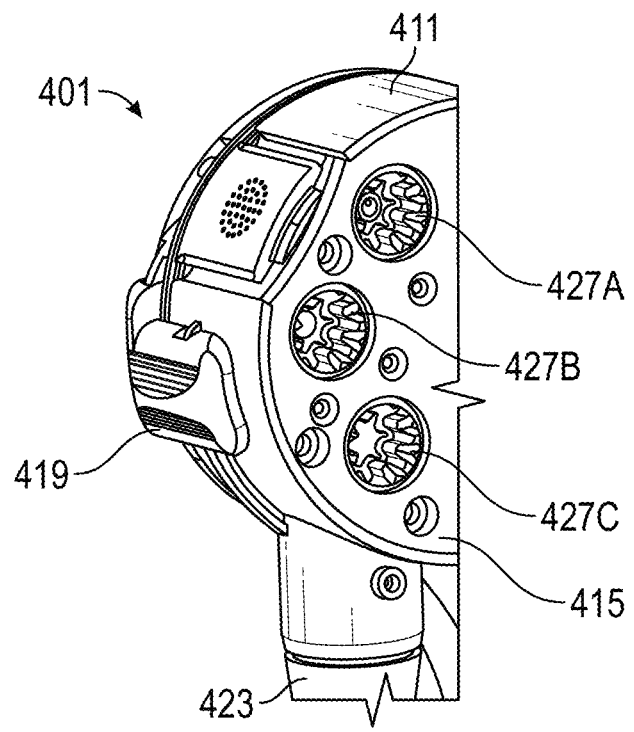

The instrument handle 401 is shown in greater detail in FIGS. 23B and 23C. FIG. 23B illustrates a first side view (e.g., a front view) of the instrument handle 401, and FIG. 23C illustrates a second, partial side view (e.g., a partial back side view) of the instrument handle 401. In some respects similar to the medical instrument 200, the instrument handle 401 is configured to allow both manual control and robotic control of the medical instrument 400. As illustrated in FIGS. 23A-23C, the instrument handle 401 includes a housing 411. The housing 411 includes a front face 413 (FIG. 23B) and a rear face 415 (FIG. 23C).

The instrument handle 401 can include a manual drive input 419. In the illustrated embodiment, the manual drive input 419 is configured as a slider. The manual drive input 419 can be configured to provide manual two-way deflection control for the medical instrument 400 as described below. In the illustrated embodiment, the manual drive input 419 is configured to be manipulated or slid back and forth along the housing 411 in the directions illustrated by the arrows 421 (FIG. 23B).

In the illustrated embodiment, the instrument handle 401 also includes a manual roll input 423. As shown in FIG. 23A, the distal end 405 of the elongated shaft 403 can be attached to the manual roll input 423. The manual roll input 423 is configured to allow the elongated shaft 403 to rotate relative to the instrument handle 401. As illustrated, the manual roll input 423 can be a twister or rotatable handle or grip that can rotate relative to the housing 411. For example, the manual roll input 423 can rotate in the directions illustrated by the arrows 425.

With reference to FIG. 23C, which show a rear view of the instrument handle 401, the medical instrument 400 includes a plurality of robotic drive inputs 427 similar to the robotic drive inputs 227 described above. In the illustrated embodiment, the medical instrument 400 includes three robotic drive inputs 427, although other numbers of robotic drive inputs 427 can be used in other embodiments. The robotic drive inputs 427 are configured to engage corresponding robotic drive outputs on an instrument drive mechanism when the instrument handle 401 is attached to the instrument drive mechanism. Example robotic drive outputs and instrument drive mechanisms are shown in FIGS. 15-17 and FIGS. 22A and 22B (described below above). The robotic drive inputs 427 can engage the robotic drive outputs as described above to transfer rotational motion between the robotic drive outputs and the robotic drive inputs 427. In the illustrated embodiment, a first robotic drive input 427a and a second robotic drive input 427b are each configured to provide two-way deflection control, such that the medical instrument 400 is capable of four-way deflection control as described previously. In some respects similar to the medical instrument 200, in some embodiments, actuation of the first robotic drive input 427a is configured to cause the same articulation of the elongated shaft 403 as actuation of the manual drive input 419.

As shown in FIGS. 23A-23C, the instrument handle 401 of the medical instrument 400 can also include a connector 431 for providing electrical and/or visual connections to the medical instrument 400. The instrument handle 401 can also include one or more latching mechanisms for orienting and securing the instrument handle to the instrument drive mechanism.

Figure 23D:
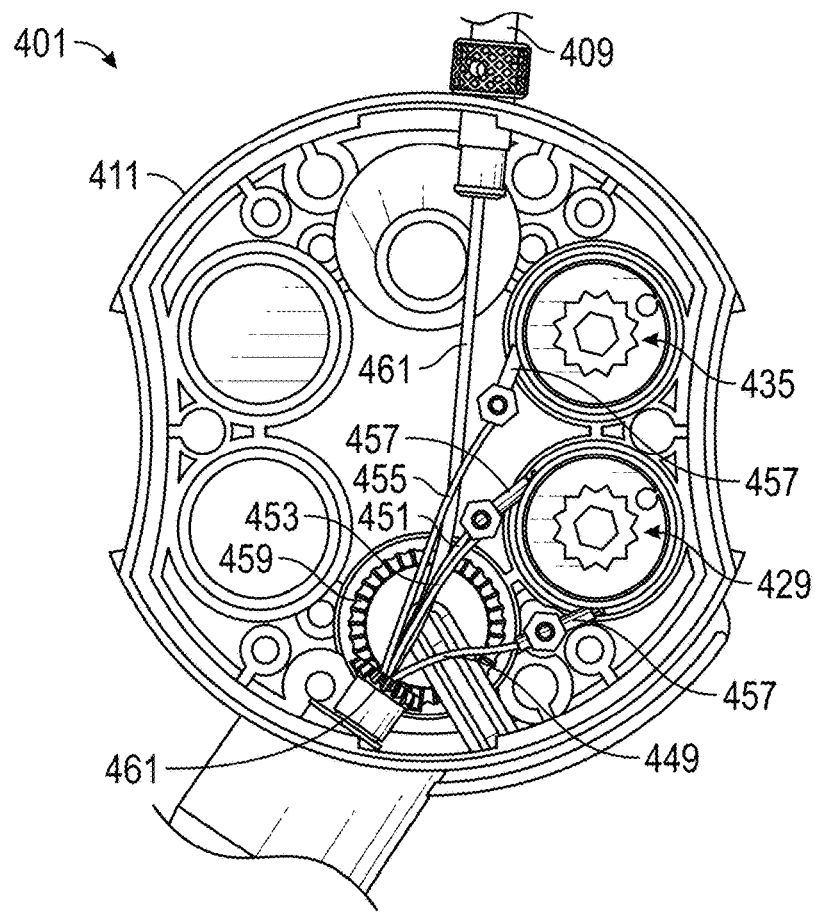
Figure 23E:
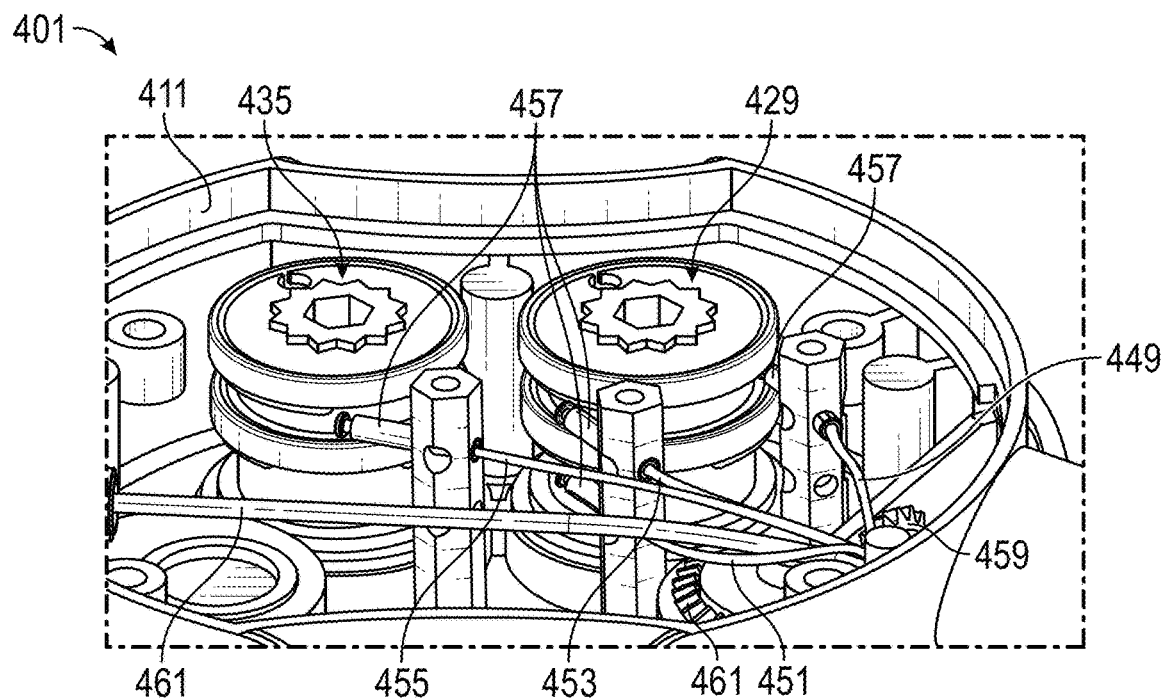

FIGS. 23D-23H illustrate some of the internal components of the instrument handle 401. FIGS. 23D and 23E illustrate first side and perspective views, respectively, of the instrument handle 401 with the front face of the housing 411 removed so as to view the internal components. As shown, two pulley assemblies, first pulley assembly 429 and second pulley assembly 435, are positioned within the housing 411. As described above, each of the first pulley assembly 429 and the second pulley assembly 435 can be associated with two of four articulation directions of the elongated shaft 403. For example, up and down articulation of the elongated shaft 403 can be associated with the first pulley assembly 429 and left and right articulation of the elongated shaft 403 can be associated with the second pulley assembly 435.

Figure 23F:
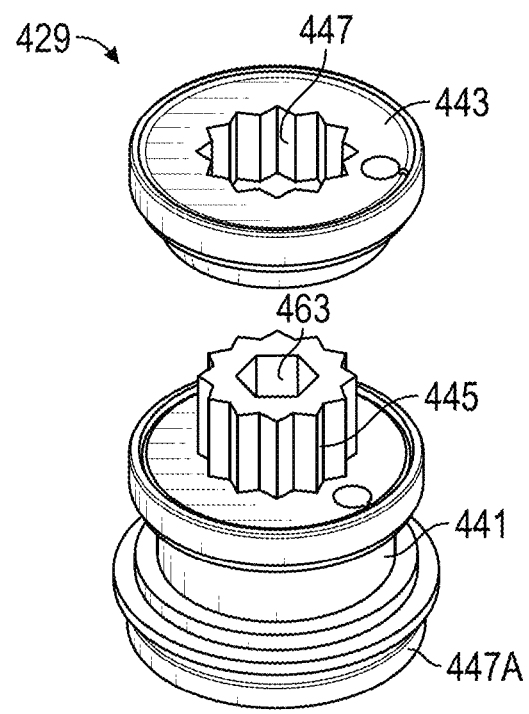

An example first pulley assembly 429 is illustrated with an exploded view in FIG. 23F. In some embodiments, the second pulley assembly 435 may be similar. As illustrated, the first pulley assembly 429 includes a first pulley 441 and a second pulley 443. The second pulley 443 can be configured to be removably attachable to the first pulley 441. When attached, the second pulley 443 and the first pulley 441 can rotate together. In the illustrated embodiment, the first pulley 441 includes a keyed portion 445 configured to engage with a keyed portion 447 on the second pulley 443. The keyed portion 445 is configured to engage the keyed portion 447 to rotationally couple the second pulley 443 to the first pulley 441 in a manner similar to that previously described. The first pulley assembly 429 can also include a keyed opening 463 for receiving a shaft 439 which can couple the first pulley assembly 429 to the manual drive input 419.

Figure 23G:
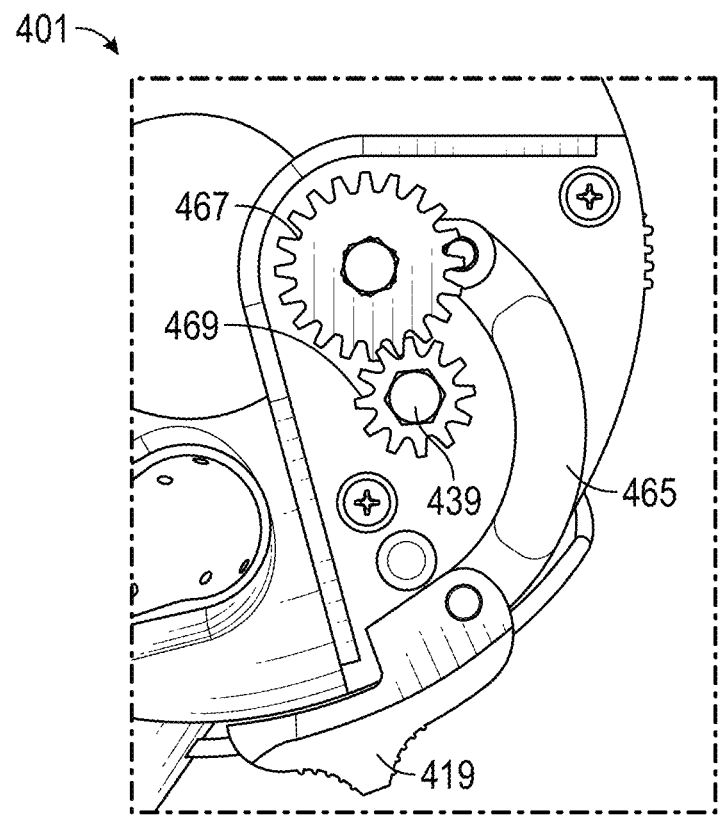
Figure 23H:
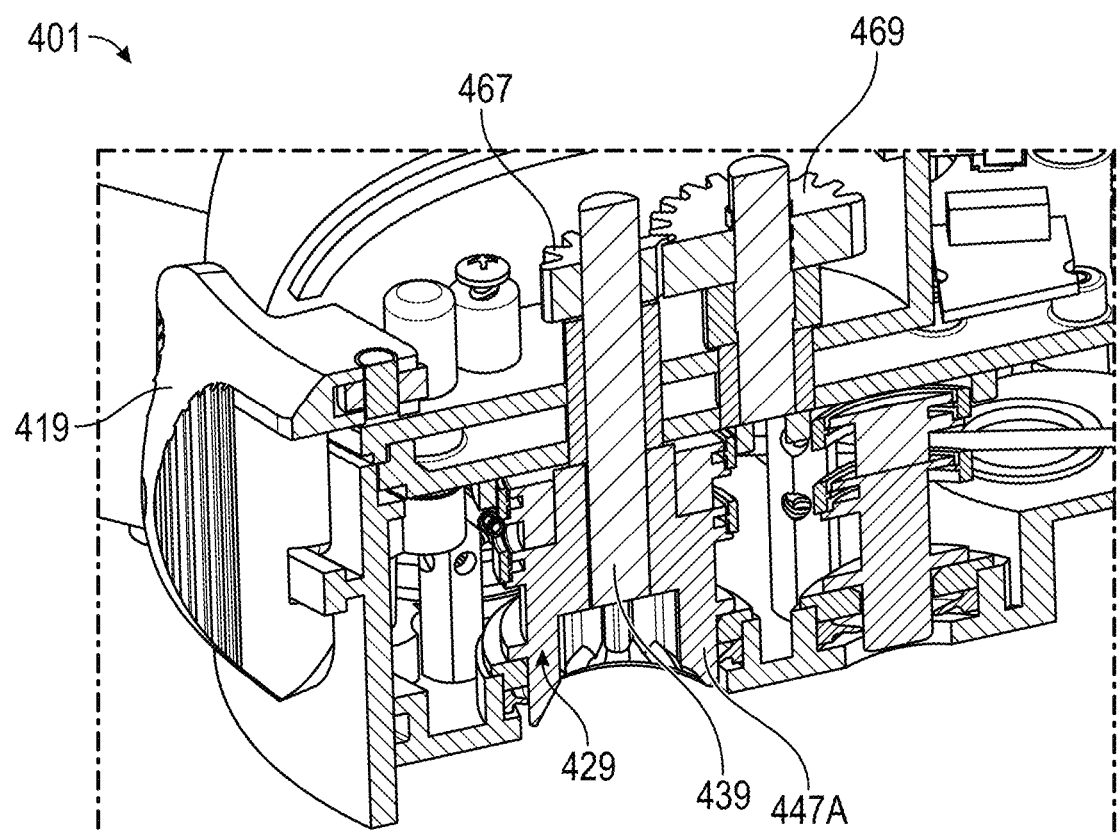

As illustrated in FIGS. 23F and 23H, one end of the first pulley assembly 429 can be connected to the first robotic drive input 427a. Thus, rotation of the first robotic drive input 427a can be configured to cause rotation of the first pulley assembly 429, including rotation of both the first pulley 441 and the second pulley 443. As best seen in FIGS. 23G and 23H, the opposite end of the first pulley assembly 429 can also be connected to the manual drive input 419. Thus, actuation of the manual drive input 419 can also be configured to cause rotation of the first pulley assembly 429, including rotation of both the first pulley 441 and the second pulley 443.

As shown in FIGS. 23G and 23H, the manual deflection input 419 can coupled to the first pulley assembly 429 such that the manual deflection input 419 can be used to cause rotation of the first pulley assembly 429. Thus, in the illustrated embodiment, both the manual drive input 419 and the first robotic drive input 427a are each coupled to the first pulley assembly 429, such that both can cause articulation of the elongated shaft 403 in, for example, the up and down directions.

In the illustrated embodiment, the manual drive input 419 is configured as a slider that is attached to the first pulley assembly 429 through an arrangement of gears and linkages as shown, for example, in FIGS. 23G and 23H. As illustrated, this arrangement can include the manual drive input 419, an intermediate link 465, an articulation drive gear 467, an articulation driven gear 469, the shaft 439, and the first pulley assembly 429. Torque input at the manual drive input 419 (by, for example, sliding the manual drive input 419 back and forth) can be transferred through the intermediate link 465, the articulation drive gear 467, the articulation driven gear 469, and the shaft 439 to the first pulley assembly 429. Articulation stroke and sensitivity can be adjusted through appropriate sizing of the articulation drive gear 467 and the articulation driven gear 469. In some embodiments, shaft bearings and seals can be included to isolate any electronics.

In the illustrated embodiment, the second pulley assembly 435 is only articulable with the second robotic drive input 427b. In some embodiments, a second manual drive input (not illustrated) can be rotationally coupled to the second pulley assembly 435 to further allow manual control of the elongated shaft in, for example, the left and right directions.

The medical instrument 400 may include pull wires for articulating the elongated shaft 403. Similar to the medical instrument 200, the pull wires can extend between the first and second pulley assemblies 429, 435 and the distal end 405 of the elongated shaft 403. The pull wires can be connected to the distal end 405 of the elongated shaft 203. At the first and second pulley assemblies 429, 435 each of the pull wires can be wound, wrapped, or otherwise mounted on or connected to the one of the pulleys of the two pulley assemblies in opposite directions as noted above. An example of this arrangement of pull wires is shown in FIGS. 23D and 23E, which show a first pull wire 449 and a second pull wire 451 wound on the first pulley assembly 429 in opposite directions and a third pull wire 453 and a second pull wire 455 wound on the second pulley assembly 435 in opposite directions.

As before, in some embodiments, the pull wires are routed to adjustable stoppers 457 that allow for fine adjustment of pull wire tension. Gross adjustment of pull wire tension is possible by selectively rotationally positioning the second pulley 443 relative to the first pulley 441 using the keyed engagement features of keyed portions 445, 447. In some embodiments, a spring can additionally or alternatively be used to apply tension to each pull wire. In some embodiments, coil pipes, not shown, extend from the adjustable stoppers 457, down through the elongated shaft 403, and to the distal end 405. The pull wires and coil pipes can include service loops (e.g., extra length) to allow for roll of the elongated shaft 403 as noted above.

As best seen in FIG. 23D, in the illustrated embodiment, robotic shaft roll can be achieved by first bevel gear 459 and a second bevel gear 461 in a manner similar to that described above. Thus, the medical instrument 400 illustrated in FIGS. 23A-23H can be configured for manual two-way deflection control, manual roll control, robotic four-way deflection control, and robotic roll control.

FIGS. 24A-24E illustrate various views of another embodiment of a manually and robotically controllable medical instrument 500. As will be described in greater detail below, the medical instrument 500 is configured for manual two-way deflection control and robotic four-way deflection control. Roll control can be achieved, in some embodiments, by rolling the entire medical instrument 500 either manually or robotically.

Figure 24A:
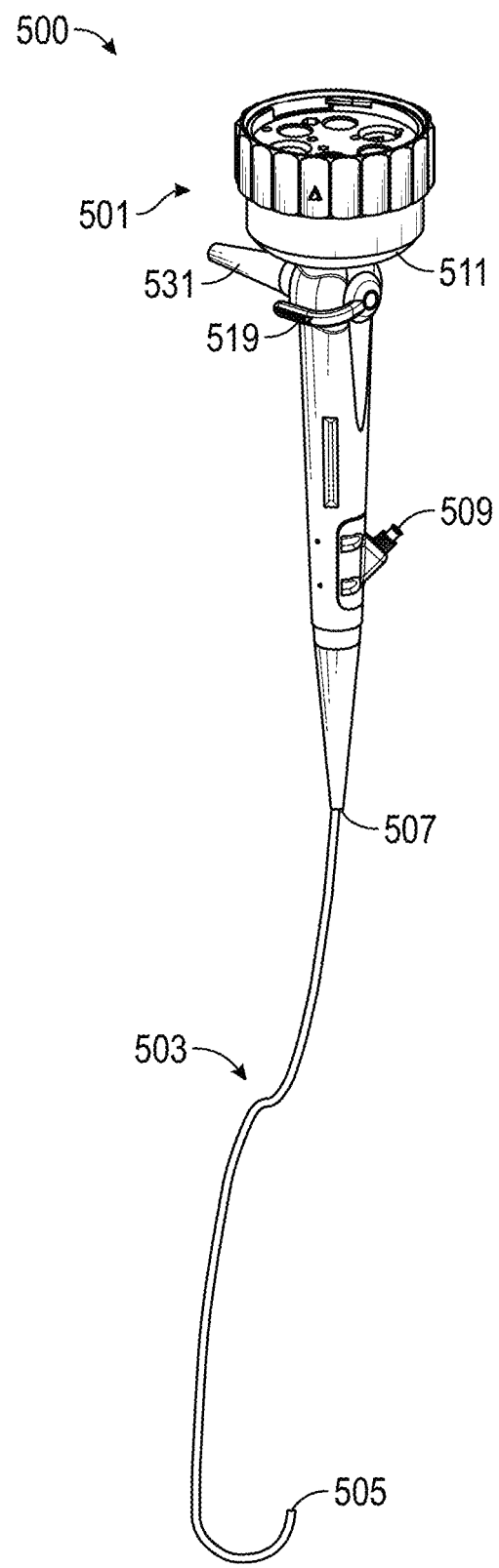

FIG. 24A illustrates a perspective view of the medical instrument 500. In some respects similar to the medical instruments 200 and 300, the medical instrument 500 includes an instrument handle 501 and an elongated shaft 503. The elongated shaft 503 can extend between a distal end 505 and a proximal end 507. The distal end 505 can be configured to be inserted into the patient. The proximal end 507 can be attached to the instrument handle 501. The elongated shaft 503 can include a working channel and an entry port 509 configured to allow access to the working channel.

Figure 24B:
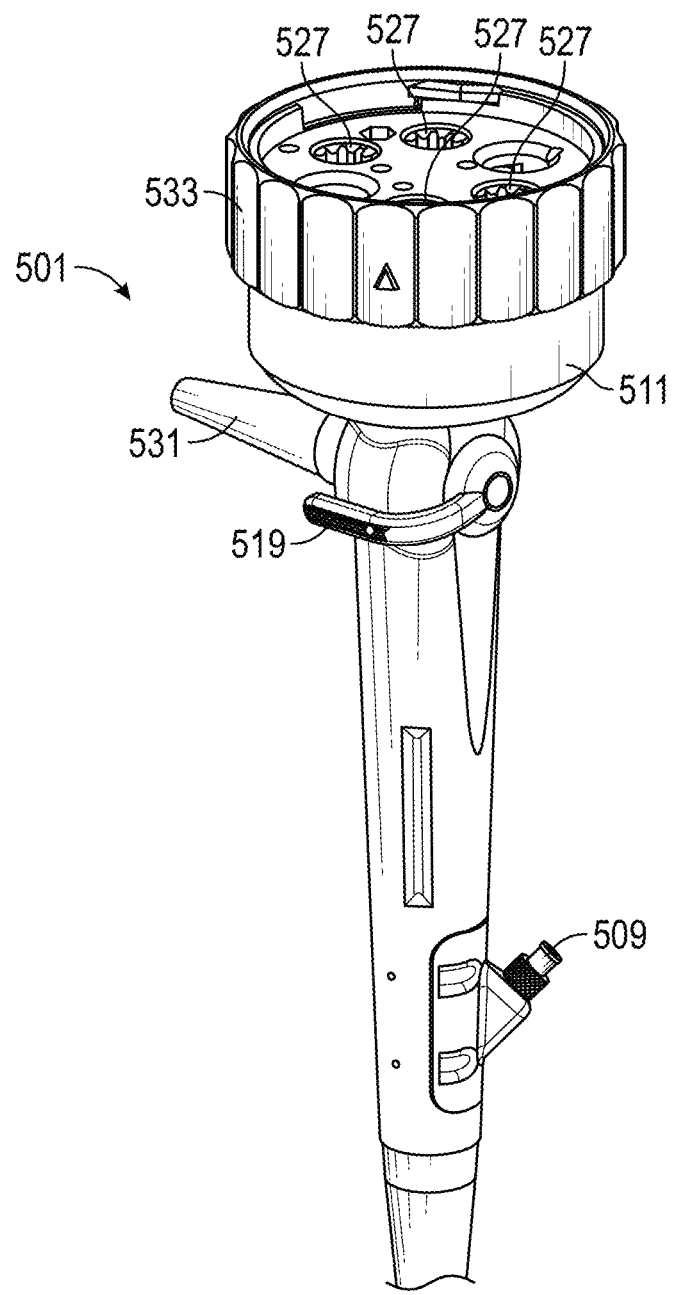

The instrument handle 501 is shown in greater detail in FIG. 24B, which illustrates a detailed perspective view of the instrument handle 501. As illustrated in FIGS. 24A and 24B, the instrument handle 501 includes a housing 511. The instrument handle 501 can include a manual drive input 519. In the illustrated embodiment, the manual drive input 519 is configured as a lever. The manual drive input 519 can be configured to provide manual two-way deflection control for the medical instrument 500. The medical instrument 500 can include a plurality of robotic drive inputs 527 similar to the robotic drive inputs 527 described above. Example robotic drive outputs and instrument drive mechanisms are shown in FIGS. 15-17 and FIGS. 22A and 22B (described below above). The robotic drive inputs 527 can engage the robotic drive outputs as described above to transfer rotational motion between the robotic drive outputs and the robotic drive inputs 527. In the illustrated embodiment, the medical instrument 500 includes four robotic drive inputs 527, although other numbers of robotic drive inputs 527 can be used in other embodiments. The robotic drive inputs 527 are configured to engage corresponding robotic drive outputs on an instrument drive mechanism when the instrument handle 501 is attached to the instrument drive mechanism. In the illustrated embodiment, each of the robotic drive inputs 527 is configured to provide deflection control in a single direction such that the medical instrument 500 is capable of four-way deflection control.

The instrument handle 501 of the medical instrument 500 can also include a connector 531 for providing electrical and/or visual connections to the medical instrument 500. The instrument handle 501 can also include one or more latching mechanisms 533 for orienting and securing the instrument handle 501 to the instrument drive mechanism.

Figure 24D:
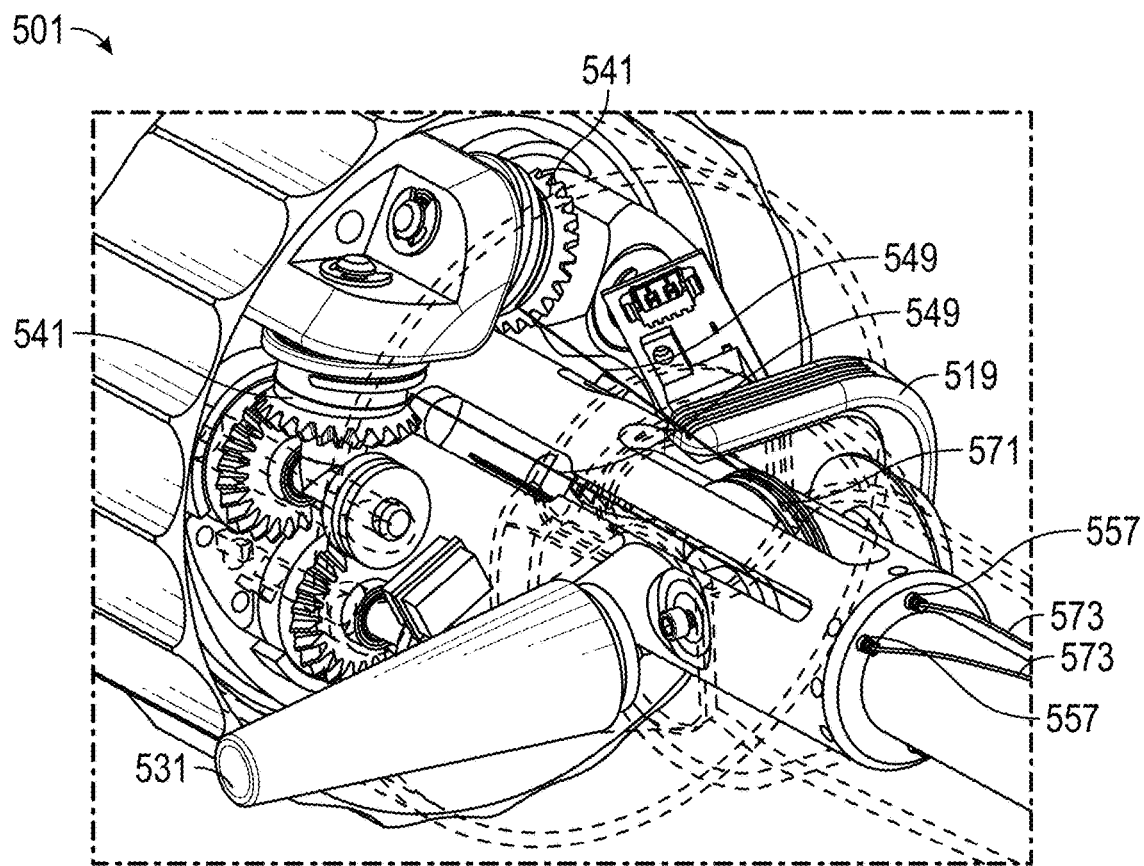
Figure 24E:
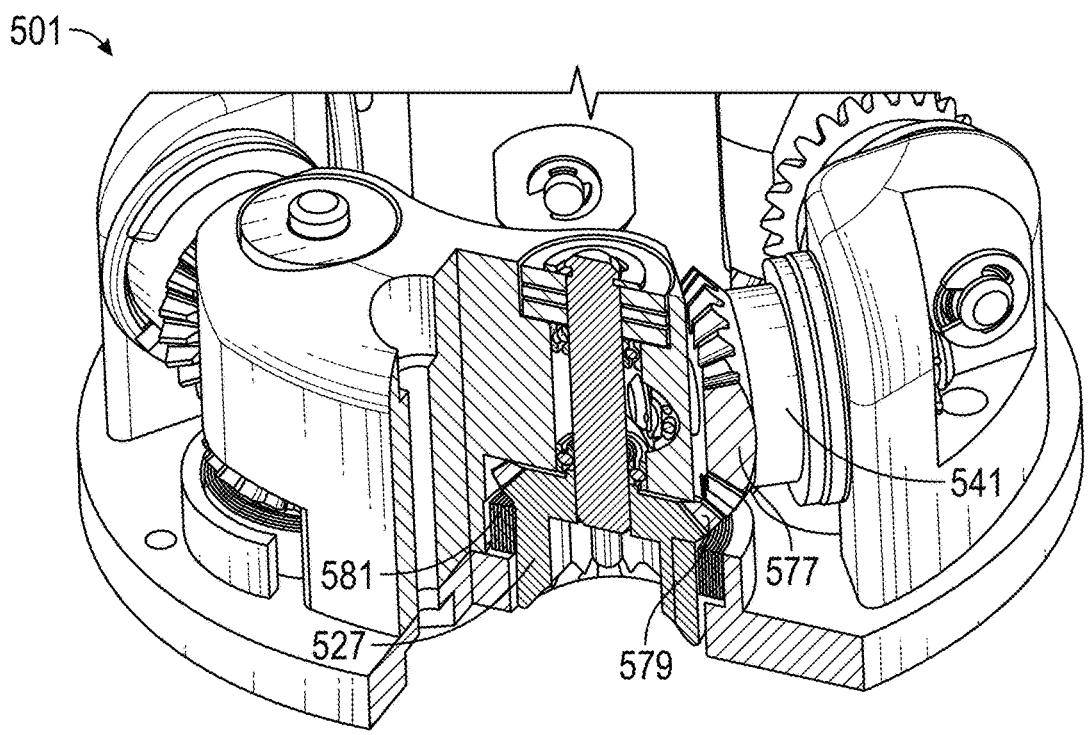

In the views of FIGS. 24C-24E the housing 511 is illustrated as transparent or removed to visualize some of the internal components of the instrument handle 501. In the illustrated embodiment, four-way robotic articulation is achieved via four pulleys 541 (FIGS. 24D and 24E). In some embodiments, each pulley 541 is associated with one of each of the four orthogonal deflection directions (e.g., up, down, left, and right). Further, each pulley 541 is coupled to one of the four robotic drive inputs 527, such that the drive inputs 527 can cause rotation of the pulleys 541 to cause articulation of the elongated shaft 503. For example, as shown in FIGS. 24D and 24E, each pulley 541 is coupled to driven gear 577, which is engaged with a drive gear 579 that is connected to the robotic drive input 527. The drive and driven gears 577, 579 can be miter or beveled gears as illustrated, although other arrangements are possible. In some embodiments, minimal constant pull wire tension is provided via torsion springs 581 engaged on the drive gears 579. Torque is transferred via drive and driven gears 577, 579 to the pulleys 547 resulting in pull wire tension being applied.

The pull wires 549 are illustrated wound on the pulleys 541 in FIG. 24D. From the pulleys 541, the pull wires extend through coil pipes 573 to the distal end of the elongated shaft. Adjustable stoppers 557 can be included to further adjust pull wire tension.

As best seen in FIG. 24D, two of the pull wires 549 can engage a manual articulation pulley 571 between the pulleys 541 and the distal end 507 of the elongated shaft 503. In some embodiments, the two pull wires 549 correspond to one plane of deflection (e.g. up/down or left/right). In some embodiments, the two pull wires fully wrap around the manual articulation pulley 571. The two pull wires engaged with the manual articulation pulley 517 can include an intermediate termination (e.g. a crimp) that engages with features on the manual articulation pulley 571. The manual drive input 519 is coupled to the manual articulation pulley 571 to cause rotation of the manual deflection pulley 571 in order to provide two-way deflection control. This can allow manual articulation via the manual drive input 519 when the handle is not connected to the robot.

In some embodiments, the medical instrument 500 can provide roll control both manually and robotically. In some embodiments, manual roll control is achieved by rotating the entire medical instrument 500 (instrument handle 501 and elongated shaft 503). In some embodiments, robotic roll control is achieved by attaching the medical instrument to an instrument drive mechanism that is configured to rotate the entire medical instrument 500 (instrument handle 501 and elongated shaft 503). In some embodiments, additional roll controls (for example, manual and robotic roll controls similar to those described above with reference to medical instruments 200 and 400 can be applied to the medical instrument 500.

Figure 25:
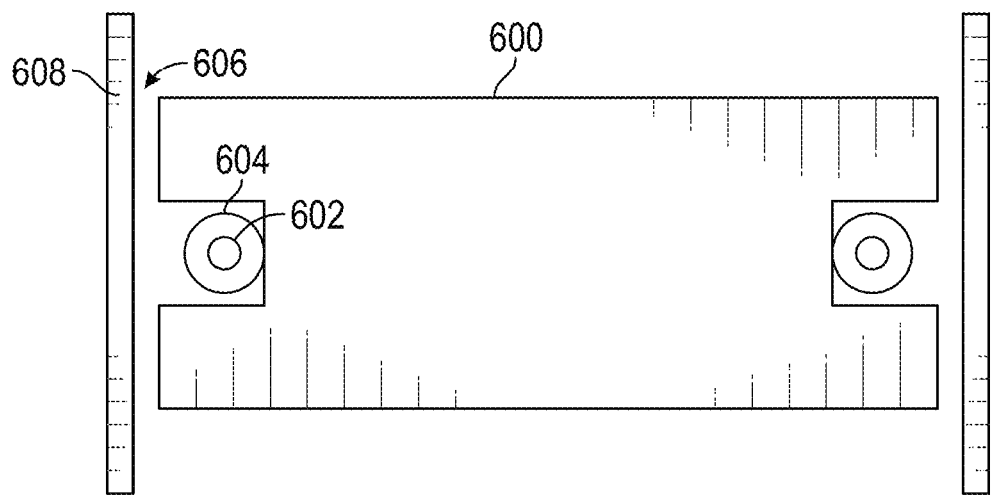
FIG. 25 illustrates a cross-sectional view of a pull wire wound on a pulley according to an embodiment.

FIG. 25 illustrates a cross-sectional view of a pull wire 602 wound on a pulley 600. In some embodiments, in the portions of the pull wire 602 that engage with the pulley 600, the diameter of the pull wire 602 can be increased to reduce the likelihood that the pull wire 602 will become disengaged from the pulley. As illustrated, a layer of shrink wrap or other coating can be applied to the pull wire 602 in these regions to increase the diameter. The diameter may be sufficiently increased such that it is larger than the space of a gap 606 between the pull wire and a housing 608. In this manner, the pull wire 602 can be retained on the pulley 600. This can be especially advantageous in medical instruments as described above which include very thin pull wires.

In some embodiments, a separate manual interface can be provided that is configured to attach to an instrument handle to allow for manual control of a medical instrument. In some embodiments, the manual interface is configured to work with medical instruments that would otherwise not be manually controllable. For example, the manual interface can be configured to attach to and actuate the robotic drive inputs (which are normally used for robotic control) to allow manual control. The manual interface can include one or more manual drive inputs that can be operated by hand. For example, the manual interface may couple manual drive inputs (e.g., levers, sliders, wheels, etc.), which are suitable for hand operation to the robotic drive inputs (e.g., spline-type rotational couplers), which may not be easily hand operable. When the manual interface is coupled to the instrument handle, a physician can operate the one or more manual drive inputs on the manual interface to manually control the medical instrument. When the manual interface is removed from the instrument handle, the instrument handle can be attached to an instrument drive mechanism that can robotically control the medical instrument. The physician can attach the manual interface to the robotic drive inputs when manual control is desired, and remove the manual interface and attach the robotic drive inputs to an instrument drive mechanism of a robotically-enabled medical system when robotic control is desired.

C. Example Methods for Controlling Manually and Robotically Controllable Medical Instruments.

Figure 26:
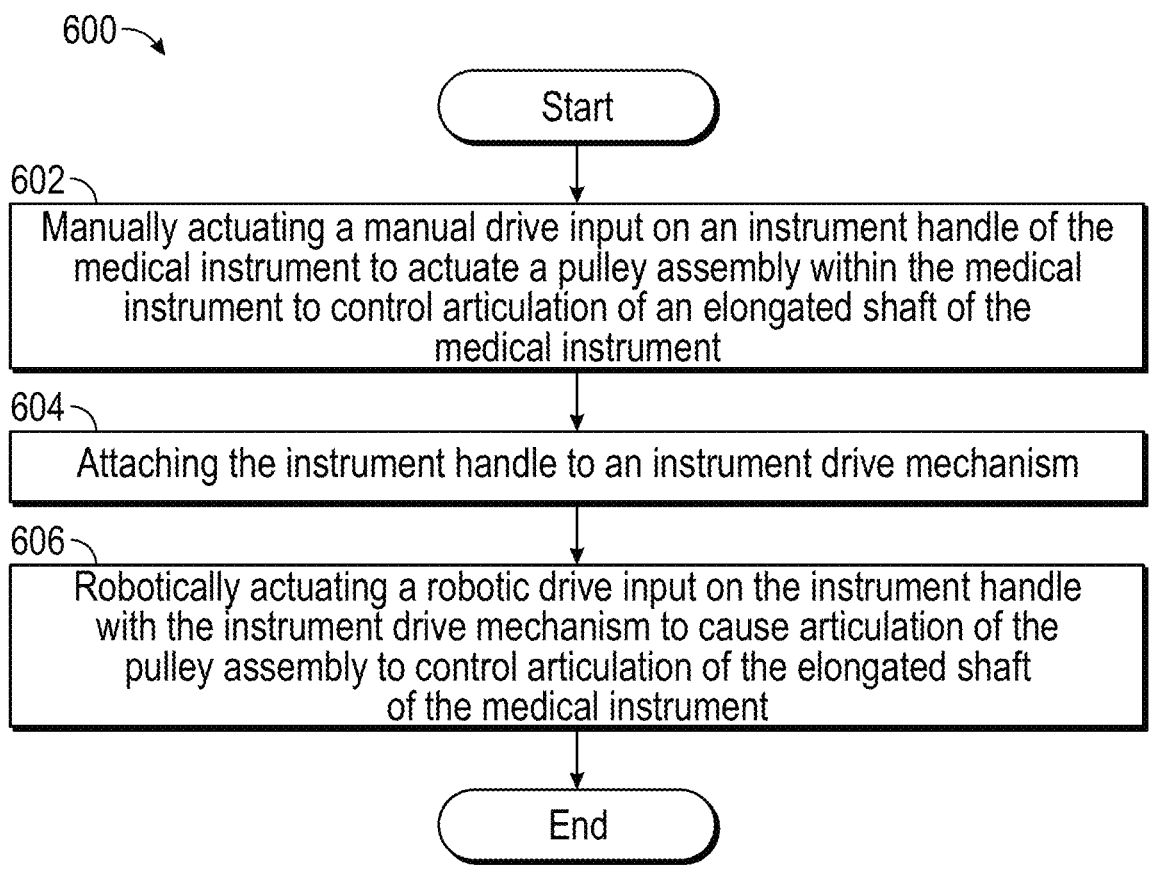
FIG. 26 is a flowchart illustrating an example of a method for controlling a medical instrument that is configured for both manual control and robotic control.

FIG. 26 is a flowchart illustrating an example method 600 for controlling a manually and robotically controllable medical instruments, such as the medical instruments 200, 400, and 500 described above. The method 600 may also be useable with other medical instruments configured for manual and robotic control.

The method 600 begins at block 602, at which a manual drive input of an instrument handle of a medical instrument is manually actuated to actuate a pulley assembly within the medical instrument to control articulation of an elongated shaft of the medical instrument.

Manually actuating the manual drive input can include manually manipulating the manual drive input to provide two-way deflection control of the elongated shaft of the medical instrument. Manually actuating the manual drive may input further include manually rotating the elongated shaft with respect to the handle to provide roll control for the elongated shaft.

In some embodiments, the manual drive input comprises a lever, a wheel, or a slider.

At block 604, the method 600 includes attaching the instrument handle to an instrument drive mechanism. Attaching the instrument handle to the instrument drive mechanism may include engaged the robotic drive input with a robotic drive output of the instrument drive mechanism.

In some embodiments, when engaged, the manual drive input may still be accessible to a user such that the manual drive input can still be used while the medical instrument is engaged. In some embodiments, the manual drive input may be inaccessible or may disengage such that it is not useable when the medical instrument is engaged with the instrument drive mechanism.

At block 606, the method 600 includes robotically actuating a robotic drive input on the instrument handle with the instrument drive mechanism to cause articulation of the pulley assembly to control articulation of the elongated shaft of the medical instrument.

Robotically actuating the robotic drive input can include robotically manipulating the robotic drive input to provide four-way deflection control of the elongated shaft of the medical instrument. Robotically actuating the robotic drive input may further include robotically manipulating the robotic drive input to provide roll control of the elongated shaft of the medical instrument.

In some embodiments, the robotic drive input comprises at least three robotic drive inputs configured to engage with at least three robotic drive outputs on the instrument drive mechanism.

3. Implementing Systems and Terminology

Implementations disclosed herein provide systems, methods and apparatus related to manually and robotically controllable medical instruments. As discussed above, the medical instruments can be controlled by manual and robotic drive inputs allowing the devices to be used both manually and robotically.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The phrases referencing specific computer-implemented processes and functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical instrument, comprising:
an elongated shaft extending between a distal end and a proximal end;
a first pull wire extending on or within the elongated shaft, the first pull wire actuable to control articulation of the elongated shaft; and
an instrument handle connected to the proximal end of the elongated shaft, the instrument handle configured to attach to an instrument drive mechanism, the instrument handle comprising:
a first pulley assembly positioned within the instrument handle, wherein the first pull wire is positioned on the first pulley assembly such that rotation of the first pulley assembly rotates the first pulley assembly about an axis of a first pulley shaft and actuates the first pull wire to cause articulation of the elongated shaft;
a first manual drive input that rotates about the axis of the first pulley shaft and is directly connected to the first pulley assembly such that manual rotation of the manual drive input about the axis of the first pulley shaft causes rotation of the first pulley assembly to cause articulation of the elongated shaft; and
a first robotic drive input, the first robotic drive input configured to engage with a first robotic drive output of the instrument drive mechanism such that rotation of the first robotic drive output causes rotation of the first pulley assembly to cause articulation of the elongated shaft without acting through the first manual drive input.

2. The medical instrument of claim 1, wherein:
the medical instrument is configured to be manually controlled by manual actuation of the first manual drive input when the instrument handle is not attached to the instrument drive mechanism, and
the medical instrument is configured to be robotically controlled by robotic actuation of the first robotic drive input when the instrument handle is attached to the instrument drive mechanism.

3. The medical instrument of claim 1, wherein the first manual drive input is separate from the first robotic drive input.

4. The medical instrument of claim 1, wherein the first manual drive input is manually accessible when the instrument handle is attached to the instrument drive mechanism.

5. The medical instrument of claim 1, wherein:
the first manual drive input is configured to provide manual two-way deflection control of the elongated shaft; and
the medical instrument is configured for four-way robotic control when the instrument handle is attached to the instrument drive mechanism.

6. The medical instrument of claim 1, wherein the first pull wire is actuable to control articulation of the elongated shaft in a first articulation direction, the first pull wire is wound on the first pulley assembly in a first winding direction, and the medical instrument further comprises:
a second pull wire extending on or within the elongated shaft, the second pull wire actuable to control articulation of the elongated shaft in a second articulation direction opposite the first articulation direction,
wherein the second pull wire is wound on the first pulley assembly in a second winding direction opposite the first winding direction.

7. The medical instrument of claim 6, wherein the first pulley assembly comprises:
a first pulley positioned on the first pulley shaft, the first pull wire wound on the first pulley; and
a second pulley positioned on the first pulley shaft, the second pull wire wound on the second pulley.

8. The medical instrument of claim 7, further comprising:
a third pull wire extending on or within the elongated shaft, the third pull wire actuable to control articulation of the elongated shaft in a third articulation direction;
a fourth pull wire extending on or within the elongated shaft, the fourth pull wire actuable to control articulation of the elongated shaft in a fourth articulation direction opposite the third articulation direction; and
a second robotic drive input configured to engage with a second robotic drive output of the instrument drive mechanism such that the rotation of the second robotic drive output causes rotation of the second pulley assembly to control articulation of the elongated shaft in the third and fourth directions.

9. The medical instrument of claim 1, further comprising a manual roll input configured to provide manual roll control of the elongated shaft.

10. The medical instrument of claim 9, wherein the manual roll input allows the elongated shaft to rotated relative to the instrument handle.

11. The medical instrument of claim 10, wherein the manual roll input comprise a rotatable handle that can rotate relative to the instrument handle.

12. The medical instrument of claim 11, further comprising a robotic roll input configured to provide robotic roll control of the elongated shaft.

13. The medical instrument of claim 1, further comprising a robotic roll input configured to provide robotic roll control of the elongated shaft.

14. The medical instrument of claim 1, wherein the first pull wire extends within a first coil pipe within the elongated shaft.

15. The medical instrument of claim 14, wherein the first pull wire and the first coil pipe include service loops to permit roll of the elongated shaft.

16. The medical instrument of claim 1, wherein the first manual drive inputs comprises at least one of a lever, a wheel, and a slider.

17. The medical instrument of claim 1, wherein the first manual drive input comprises a pivot-based movement and the first robotic drive input comprises a rotational movement.

18. The medical instrument of claim 1, wherein the first pulley assembly and the first manual drive input are both directly connected to the first pulley shaft.

\* \* \* \* \*